(12) United States Patent
Abou-Nemeh

(10) Patent No.: US 7,335,248 B2
(45) Date of Patent: Feb. 26, 2008

(54) MARINE ANTIFOULING COATING COMPOSITIONS

(75) Inventor: Ibrahim Abou-Nemeh, Lake St. Louis, MO (US)

(73) Assignee: Novus International, Inc., St. Louis, MO (US)

( * ) Notice: Subject to any disclaimer, the term of this patent is extended or adjusted under 35 U.S.C. 154(b) by 0 days.

(21) Appl. No.: 11/469,702

(22) Filed: Sep. 1, 2006

(65) Prior Publication Data

US 2007/0213426 A1 Sep. 13, 2007

Related U.S. Application Data

(60) Provisional application No. 60/714,436, filed on Sep. 6, 2005.

(51) Int. Cl.
*C09D 5/16* (2006.01)
*A01N 31/02* (2006.01)
*A01N 33/00* (2006.01)
*C23F 15/00* (2006.01)

(52) U.S. Cl. ............... 106/18.34; 106/15.05; 106/18.36; 424/78.09; 427/384; 427/385.5; 428/357; 514/492; 514/494; 514/500; 514/501; 514/502; 514/706; 523/177

(58) Field of Classification Search ............ 106/15.05, 106/18.34, 18.36; 424/78.09; 427/384, 427/385.5; 428/357; 514/492, 494, 500, 514/501, 502, 706; 523/177
See application file for complete search history.

(56) References Cited

U.S. PATENT DOCUMENTS

| | | | |
|---|---|---|---|
| 3,941,818 A | 3/1976 | Abdel-Monem | |
| 4,579,962 A * | 4/1986 | Takano | 556/131 |
| 4,855,495 A * | 8/1989 | Takano | 562/581 |
| 4,863,898 A | 9/1989 | Ashmead et al. | |
| 5,386,056 A * | 1/1995 | Matsuoka | 562/526 |
| 5,583,243 A | 12/1996 | Abdel-Monem | |
| 5,932,454 A * | 8/1999 | Matsuoka et al. | 435/130 |
| 6,242,009 B1 | 6/2001 | Batarseh et al. | |
| 6,306,201 B1 | 10/2001 | Makino | |
| 6,461,664 B1 | 10/2002 | Ciribolla | |
| 6,531,101 B2 * | 3/2003 | Hsu et al. | 422/187 |
| 6,627,773 B1 * | 9/2003 | Ikudome et al. | 562/581 |
| 6,649,794 B2 * | 11/2003 | Ikudome et al. | 562/580 |
| 2007/0053866 A1 * | 3/2007 | Abou-Nemeh | 424/78.09 |

FOREIGN PATENT DOCUMENTS

DE 4338923 A1 * 5/1995
JP 200247266 A * 2/2002

* cited by examiner

*Primary Examiner*—Anthony J. Green
(74) *Attorney, Agent, or Firm*—Polsinelli Shalton Flanigan Suelthaus PC

(57) ABSTRACT

Disclosed are marine coating compositions that are useful to inhibit the fouling of a marine structure by a broad spectrum of organisms. Generally, the marine coating composition comprises an antifouling agent and an organic vehicle.

87 Claims, 10 Drawing Sheets
(10 of 10 Drawing Sheet(s) Filed in Color)

12-month Static Immersion In The Indian Ocean

Control- copper ablative paint (CuAB)

12-month Static Immersion In The Indian Ocean

5% HMTBA-Cu in copper ablative paint (CuAB)

12-month Static Immersion In The Indian Ocean

5% HMTBA-Zn in copper ablative paint CuAB 12-month Static Immersion In The Indian Ocean Control - Copper self-polishing paint (CuSP)

12-month Static Immersion In The Indian Ocean

5% HMTBA-Cu in copper self-polishing paint (CuSP)

12-month Static Immersion In The Indian Ocean

5% HMTBA-Zn in copper self-polishing paint (CuSP)

5-MONTH SIT IN LAKE ERIE, USA

UNPAINTED
CONTROL

5% HMTBA-Zn
in copper self-polishing
paint (CuSP)

5-MONTH SIT IN LAKE ERIE, USA

UNPAINTED
CONTROL

5% HMTBA-Cu
in copper ablative
paint (CuAB)

5-MONTH SIT IN LAKE ERIE, USA

UNPAINTED
CONTROL

5% HMTBA-Zn
in copper ablative
paint CuAB

MARINE ANTIFOULING COATING COMPOSITIONS

CROSS-REFERENCE TO RELATED APPLICATION

This application claims priority from Provisional Application Ser. No. 60/714,436 filed on Sep. 6, 2005, which is hereby incorporated by reference in its entirety.

FIELD OF THE INVENTION

The present invention generally relates to marine coating compositions comprising an antifouling agent. The antifouling agent comprises a metal chelate or a metal salt.

BACKGROUND OF THE INVENTION

Marine organisms such as algae, mollusks, tubeworms and barnacles attach to the surfaces of structures submerged in seawater, oceans, rivers and lakes. This marine growth on these surfaces may affect the integrity of the structure (e.g., ships, boats, pilings, water intake and outfall pipes) and can seriously hamper the operation of these systems. For example, on ship hulls the attachment of marine growth adversely affects the speed of the ship and its fuel efficiency due to the increased drag caused by the marine growth. For water intakes, there is an attendant loss of cooling efficiency in power generation and manufacturing process operation when such intakes have significant marine growth attached.

It has been common practice to coat the substrate surfaces of wood, plastic and metal with coating compositions that inhibit attachment and/or growth of marine organisms. Such coating compositions are usually referred to as antifoulant coatings or antifoulant paints and generally consist of a binder material, an antifouling agent (biocides and "booster biocides"), diluents and additives to aid in adhesion, flow, color, viscosity, stability, etc.

There is a concern for the possible effects of antifoulant compounds on the environment. One approach is the development and use of systems which attempt to control fouling through surface modification; for example, preventing attachment of algae and barnacles through the use of silicon or fluorine containing polymers having non-stick or release properties. Another approach is to use antifouling compounds that are toxic enough to marine life so that marine structures are not significantly fouled, but have a toxicity such that generally marine life is not harmed nor irreversibly altered. In this context, it is preferred that the compounds used as antifouling agents do not build up in the environment and cause deformation or adverse changes in marine life. It is desirable, for example, to provide antifouling agents that are less toxic than tributyltin (TBT) that has been used as an antifouling agent for many years and is now officially banned in some waters due to the harm to marine life that resulted from TBT leaching into the waters. In addition, TBT has caused deformations in oysters to develop thick shells and sex-changing disorders in whelks among other biological changes noted from its use.

Accordingly, a need exists for a wider variety of environmentally safe and effective antifouling marine coating compositions.

SUMMARY OF THE INVENTION

Among the various aspects of the present invention is a marine coating composition comprising a metal chelate or a metal salt that minimizes biofouling and is less toxic to the environment than certain previously available antifouling agents.

Briefly, therefore, the present invention is directed to a marine coating composition comprising an antifouling agent and an organic vehicle. The antifouling agent comprises a metal chelate or a metal salt. The metal chelate may comprise metal ions and ligands wherein a compound of formula 1 is a source of the ligands. The metal salt may comprise metal ions and anions wherein a compound of formula 1 is a source of the anions. The compound of formula 1 has the structure

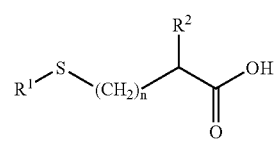

wherein:
  n is an integer from 0 to 2;
  $R^1$ is methyl or ethyl; and
  $R^2$ is selected from the group consisting of hydroxyl and amino.

Another aspect of the invention comprises a method of minimizing fouling of marine structures comprising applying a marine coating composition comprising an antifouling agent and an organic vehicle to such structures. The antifouling composition comprises a metal chelate or a metal salt. The metal chelate may comprise metal ions and ligands wherein a compound of formula 1 is a source of the ligands. The metal salt may comprise metal ions and anions wherein a compound of formula 1 is a source of the anions. The compound of formula 1 has the structure defined above.

Yet another aspect of the invention is a marine structure comprising a structural element treated with a marine coating composition comprising an antifouling agent and an organic vehicle. The antifouling agent comprises a metal chelate or metal salt. The metal chelate may comprise metal ions and ligands wherein a compound of formula 1 is a source of the ligands. The metal salt may comprise metal ions and anions wherein a compound of formula 1 is a source of the anions. The compound of formula 1 has the structure defined above.

Other aspects and features will be in part apparent and in part pointed out hereinafter.

BRIEF DESCRIPTION OF THE DRAWINGS

The application file contains at least one photograph executed in color. Copies of this patent application publication with color photographs will be providing by the Office upon request and payment of the necessary fee.

FIGS. 4(a)-(c) depict photographic images illustrating the anti-fouling activity of (a) a negative control and 5% HMTBA-Cu, and (b) a negative c control and 5% HMTBA-Zn in CUAB paint.

DETAILED DESCRIPTION OF THE INVENTION

Figure 1A:
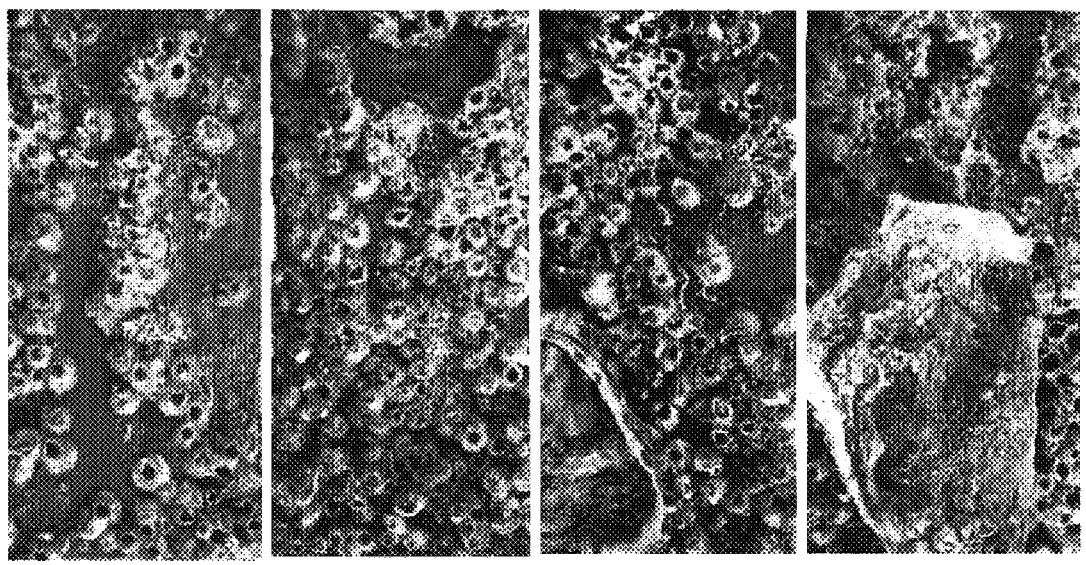
FIGS. 1(a)-(c) depict photographic images illustrating the anti-fouling activity of (a) a negative control, (b) 5% HMTBA-Cu and (c) 5% HMTBA-Zn in CUAB paint.

In accordance with the present invention, it has been discovered that a class of metal chelate or metal salt compounds is effective as an active ingredient for preventing fouling and sliming of submersed structures by various organisms and is less toxic to the environment than many of the toxicants that are conventionally used in marine coatings. This may be due, in part, to the fact that these antifouling agents are natural products, i.e., they occur in nature. Generally, these active metal chelates or metal salts can be usefully included in marine coating compositions to control or prevent attachment by barnacles, algae or similar organisms. Further, they can be applied to underwater marine structures as described below.

Typically, marine coating compositions of the present invention include an antifouling agent and an organic vehicle. Generally, the organic vehicle can be selected from a resin, a diluent and combinations thereof. Exemplary resins can be natural or synthetic resins, and can comprise solid or semisolid viscous substances that either are obtained as exudations from certain plants or are prepared by polymerization of simple molecules. Exemplary diluents are organic solvents. The marine coating compositions optionally contain additives such as pigments, fillers, swelling agents, wetting agents, biocides and combinations thereof. Suitable resins, diluents and additives are described in more detail below.

Further, the preferred marine coating compositions of the present invention have desirable mechanical properties such that when the composition dries into a marine coating, the coating has a uniform surface that is flexible and resists cracking, peeling or other deformity. The preferred marine coatings of the present invention release the antifouling agent from the matrix at a rate that is sufficient to minimize fouling of the underwater structure for a desired period of time.

Without limiting the invention to a particular theory or theories, there are understood to be at least three general mechanisms of release of the antifouling agent from the marine coating. These mechanisms differ depending on the identity of the resin contained in the marine coating. For example, one type of marine coating includes self-polishing copolymers (SPC). They were developed in the 1970s and rapidly became the most important type of antifouling coatings. The self-polishing copolymers such as copper or zinc acrylates react with saltwater in a controlled way—through hydrolysis reactions or ion exchange mechanism depending on the metallic chelate used—to sustain release of antifouling agents throughout the lifetime of the coating composition. Typically, self-polishing copolymers have pendent groups that stabilize the otherwise water-dispersible polymer against degradation in the aqueous environment. However, the pendent groups are attached to the polymer backbone by hydrolyzable linkages. Cleavage of these pendent moieties destabilizes the polymer molecule and renders it susceptible to dispersion in the aqueous environment. Thus, polymer molecules progressively wash away from the film surface at rate determined by the rate at which pendent groups are hydrolytically cleaved from the polymer backbone. As this process proceeds, antifouling agent contained within the polymer film matrix is exposed to the aqueous medium, thereby inhibiting attachment of marine organisms to the surface. Pendent groups of the copolymer may also be selected to balance the hydrophilic vs. hydrophobic properties of the polymer, which may also affect the rate at which polymer molecules are progressively removed from the polymer film surface in the aqueous environment.

Another type of marine coating composition includes controlled solubility polymers (e.g., ablative). The soluble matrix coatings utilize rosin or synthetic resins. These polymers are partially soluble and, consequently, as water passes across the surface of the coating, the polymers dissolve very slowly in the slightly alkaline conditions of seawater so that the coating is gradually washed away at its exterior to continually expose antifouling agents at the surface of the coating that remains. Copper-based compounds, such as cuprous oxide, thiocyanates etc. are usually the main biocides. In this type of coating the mechanical property is rather brittle and easily damaged, and the release rate of copper decreases over time.

A third type of marine coating includes contact leaching paints that are porous films wherein antifouling agents leach out on contact with water, but the film is resistant to abrasion and rubbing. Each of these types of coatings is discussed in more detail below.

A. Antifouling Agents
(i) Metal Chelates and Metal Salts

The marine coating compositions and marine coatings of the present invention contain an antifouling agent. In exemplary embodiments, the antifouling agent is a natural product, i.e., the antifouling agent may be found in nature. One class of active ingredients effective for inhibiting fouling and sliming of submersed structures (i.e., antifouling agents) comprises a metal chelate or a metal salt. In some embodiments, the metal chelate comprises metal ions, and an amino acid ligand. The metal ions may be selected from the group consisting of zinc ions, copper ions, manganese ions, iron ions, chromium ions, silver ions, cobalt ions, calcium ions and combinations thereof. In a preferred embodiment, the metal ions are zinc ions or copper ions. The amino acids may be selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the copper and zinc ions are preferably divalent, i.e., it carries a charge of $2^+$. The ratio of amino acids to metal ions in the chelate molecule may generally vary from 1:1 to 3:1 or higher. Typically, a metal chelate may comprise a mixture of 1:1, 2:1 and 3:1 species. Preferably, the ratio of amino acids to metal ion in the chelate molecule may generally vary from 1.5:1 to 2.5:1. In an aqueous medium, the relative proportions of these species are determined by the applicable stability constants.

Where the number of ligands equates to the charge on the metal ion, the charge is typically balanced because the carboxyl moieties of the amino acids are in deprotonated form. For example, in the chelate species wherein the metal cation carries a charge of $2^+$ and the amino acid to metal ratio is 2:1, each of the hydroxyl or amino groups is understood to be bound by a coordinate covalent bond to the metal while an ionic bond prevails between each of the carboxylate groups and the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, dihydrogen phosphate and combinations thereof. Divalent anions may also be present.

In an exemplary embodiment, the metal chelate comprises metal ions and ligands wherein a compound of formula 1 is a source of the ligands. The metal salt comprises metal ions and anions wherein a compound of formula 1 is a source of the anions. The compound of formula 1 has the structure

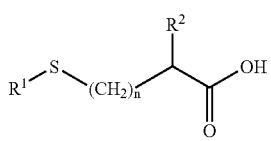

1 wherein n is an integer from 0 to 2;

$R^1$ is methyl or ethyl; and $R^2$ is selected from the group consisting of hydroxyl and amino.

In various preferred embodiments of the present invention, n is 2, $R^1$ is methyl and $R^2$ is hydroxyl (i.e., 2-hydroxy-4-methylthio-butanoic acid). Preferably, the metal ions are selected from the group consisting of zinc ions, copper ions, manganese ions, iron ions, chromium ions, silver ions, cobalt ions, calcium ions and combinations thereof. Where the metal ion is copper, manganese, chromium, calcium, cobalt and iron, it is preferably divalent, i.e., it carries a charge of $2^+$. More preferably, the metal ion comprises zinc. In an alternate preferred embodiment, the metal ion comprises copper.

In various preferred embodiments of the invention, the compound of formula 1 comprises 2-hydroxy-4-methylthiobutanoic acid ("HMTBA"), i.e., n is 2, $R^1$ is methyl and $R^2$ is hydroxyl. In particularly preferred embodiments, the metal ion is copper, zinc, calcium or manganese. Where the metal ion is copper or manganese, it is preferably divalent, i.e., it carries a charge of $2^+$. Zn cations are essentially universally divalent. In other metal chelates useful in the compositions and methods of the invention, the metal ions are also preferably divalent. The ratio of ligands to metal ion in the chelate molecule may generally vary from 1:1 to 3:1 or higher. Typically, a metal chelate may comprise a mixture of 1:1, 2:1 and 3:1 species. Preferably, the ratio of ligands to metal ion in the chelate molecule may generally vary from 1.5:1 to 2.5:1. In an aqueous medium, the relative proportions of these species are determined by the applicable stability constants. In the case where n is 2, $R^2$ is amino and $R^1$ is methyl, i.e., where the compound of formula 1 is methionine, a number of the stability constants are available from the literature. At least some stability constants may also be available for the chelates in which n is 2, $R^2$ is hydroxyl and $R^1$ is methyl, i.e., where the compound of formula 1 is HMTBA.

Where the number of ligands equates to the charge on the metal ion, the charge is typically balanced because the carboxyl moieties of the ligands are in deprotonated form. Thus, in these chelates, each of the ligands corresponds to formula 1A

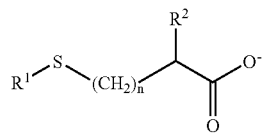

1A wherein $R^1$, $R^2$ and n are as defined above, i.e., the chelate in this respect is also a dicarboxylate salt. For example, in the chelate species wherein the metal cation carries a charge of $2^+$ and the ligand to metal ratio is 2:1, each of the hydroxyl or amino group ($R^2$) groups is understood to be bound by a coordinate covalent bond to the metal while an ionic bond prevails between each of the carboxylate groups and the metal ion. Typical examples are the complexes of $Zn^{2+}$, $Cu^{2+}$, $Mn^{2+}$ with two 2-hydroxy-4-methylthiobutanoate ions. Where the number of ligands exceeds the charge on the metal ion, e.g., in a 3:1 chelate of a divalent metal ion, the ligands in excess of the charge typically may remain in a protonated state to balance the charge. On the other hand, where the positive charge on the metal ion exceeds the number of ligands, the charge may be balanced by the presence of another anion such as, for example, chloride, bromide, iodide, bicarbonate, hydrogen sulfate, dihydrogen phosphate and combinations thereof. Divalent anions may also be present.

Metal salts wherein the metal has a $1^+$ or $2^+$ charge may also be used. These salts form when the metal, metal oxide, metal hydroxide or metal salt (e.g. metal carbonate, metal nitrate or metal halide) reacts with one or more compounds having the structure of Formula 1 to form an ionic bond between the metal and the resulting anion. Generally, these metal salts can be prepared by contacting a metal ion source with HMTBA. Preferably, a silver salt is used wherein a silver ion having a $1^+$ charge reacts with HMTBA to form a silver $2^-$-hydroxy-4-methylthiobutanoate metal salt. Generally, this silver metal salt has a silver to 2-hydroxy-4-methylthiobutanoate ratio comprising 1:1. This silver metal salt can be prepared by contacting silver nitrate or silver chloride with HMTBA. Antifouling agents comprising other metals may also be in the form of salts. Without being bound to a particular theory, it is believed that combinations of Zn, Cu, Mn, Fe, Cr, Ni and Co ions with HMTBA are primarily in the form of chelates.

The metal chelates of the present invention can be prepared generally according to the methods described in U.S. Pat. Nos. 4,335,257 and 4,579,962. In a preferred preparation process, a metal source compound such as a metal oxide, a metal carbonate or a metal hydroxide is charged to a reaction vessel, and an aqueous solution of HMTBA is added to the source compound. The concentration of HMTBA in the aqueous solution is preferably between about 40% and about 89% or more by weight. Reaction typically proceeds over a period of 2 hours under moderate agitation. Water and/or carbon dioxide is produced in the reaction depending on the starting material. Ordinarily, the reaction is conducted substantially at atmospheric pressure, and the reaction mass is heated to a temperature in the 90° to 130° C. range for removal of water.

After the reaction is substantially complete, heating of the reaction mass is continued in the reaction vessel to produce a substantially dried product. Ultimately, the free water content is reduced to about 2% by weight, and the product mass transitions to free-flowing particulate solid. The dried metal chelate product may optionally be mixed with a calcium bentonite filler and ground to a powder.

Where the carboxyl of the ligand is in deprotonated form, each of the ligands and the metal ion is believed to form a five membered ring, so that the 2:1 species has the structure:

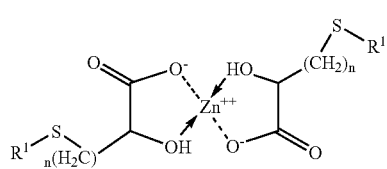

The concentration of antifouling agent may vary substantially depending on the nature of the marine structure to which the coating composition is applied, the service in which the marine structure is used, the body of water and other environmental conditions to which the marine structure is exposed, etc. Generally, the concentration of antifouling agent is sufficient to reduce fouling compared to that incurred in the presence of marine organisms at the same location and under the same conditions by an identical structure that is coated with a paint of identical composition except for the absence of a metal chelate, metal salt or other antifouling agent from the paint composition. Typically, the metal chelate or metal salt concentration in the marine coating composition is from about 0.05 wt. % to about 50 wt. %. Preferably, the metal chelate or metal salt concentration in the marine coating composition can be from about 0.1 wt. % to about 25 wt. %. More preferably, the metal chelate or metal salt concentration in the marine coating composition can be from about 1 wt. % to about 10 wt. %. But, the optimal metal chelate or metal salt concentration in the marine coating composition is dependent on the type of marine coating in which the metal chelate or metal salt is incorporated. For example, metal chelates or metal salts may tend to be leached out of a marine coating when subjected to prolonged exposure to seawater, lake water or river water. However, different kinds of marine paints have different degradation rates and consequently, the leaching rate of the metal chelate or metal salt from the paint may differ. But regardless of the leaching rate, the concentration of the metal chelate or metal salt in the marine coating is preferably low enough so the coating properties of uniformity, thickness and continuity are not unduly affected. As discussed below, these variables of leaching and coating properties may appropriately be considered when determining the optimum concentration of the metal chelate or metal salt in the marine coating composition.

In some cases, the particle size of the antifouling agent is important. For example, a commercially available copper 2-hydroxy-4-methylthiobutanoate chelate has been found to have a grain size that is too large to produce a smooth, even dispersion in the marine coating matrix. In this case, the solid granular chelate was ground mechanically to smaller particle sizes. In general, where the particle size of the chelate is considered too coarse for a specific application, it may be ground mechanically to a smaller particle size. To achieve a highly uniform dispersion of extended stability, and or to provide a smooth even finish, it may be desirable to reduce the metal chelate or metal salt to an average particle size of less than about 800 microns, more preferably to an average particle size in the range of about 700 to about 100 microns e.g., an average particle size of about 400 microns wherein at least about 95 wt. % of the particles average an average size between about 50 and about 800 microns.

In various embodiments of the present invention, the mean particle size of the metal chelate or metal salt is from about 700 μm to about 100 μm; preferably, from about 600 μm to about 200 μm. The particle size may depend in part on the antifouling agent used. For instance, a zinc 2-hydroxy-4-methylthiobutanoate chelate provides a uniform dispersion of extended stability at a larger particle size than a copper 2-hydroxy-4-methylthiobutanoate chelate. In some embodiments, the zinc 2-hydroxy-4-methylthiobutanoate chelate particle size is from about 700 μM to about 200 μM; preferably, from about 600 μM to about 300 μM, more preferably from about 500 μM to about 400 μM. In other embodiments, the copper 2-hydroxy-4-methylthiobutanoate chelate particle size is from about 600 μM to about 100 μM; preferably, from about 500 μM to about 200 μM, more preferably from about 400 μM to about 300 μM.

Alternatively, in other embodiments of the invention, it may be desirable to reduce the metal chelate or metal salt to an average particle size of less than about 10 microns, more preferably to an average particle size in the range of about 0.2 to about 5 microns, e.g., an average particle size of about 2 microns wherein at least about 95 wt. % of the particles average an average size between about 0.05 and about 8 microns.

In various embodiments of the present invention, the mean particle size of the metal chelate or metal salt may be from about 0.5 μm to about 10 μm; preferably, from about 0.5 μm to about 7 μm; more preferably, from about 0.5 μm to about 2 μm; even more preferably, from about 0.5 μm to about 1 μm. Methods of determining the appropriate particle size for a given antifouling agent are well known in the art.

The antifouling agent can be included in the marine coating composition neat as a particulate solid, in an encapsulated particulate form, for example, in which individual chelate particles are embedded in a matrix of bentonite or silica, or as a suspension in a liquid medium, typically an organic liquid medium.

Generally, an encapsulated particulate form provides for a "controlled mode of release" of a toxicant or antifouling agent from the paint matrix. Typically, the encapsulation methods are directed to hydrophobic or sparingly soluble antifouling agents that are in the liquid state. However, these methods, in principle, can be applied to other types of molecules as well.

Specifically, one method of encapsulation is by incorporation of chelate particles in microtubules; this technology is described by R. R. Price & J. M. Schnur (*J. of Coatings Technology*, Vol 75, No. 943, 2003). Another method of encapsulation uses clathrate compounds and is described by Kazunobu (*Proc. Of Emerging Non-metallic Materials for Marine Environment*, Honolulu, Hi. March 18-20 pp. 1,81-1,87 (1997)). Further, yet another method of encapsulation is described by Beck and Sundberg (*Proc. Of Emerging Non-metallic Materials for Marine Environment*, Honolulu, Hi. March 18-20 pp. 3-65, 3,71 (1997)) for hydrophobic marine antifoulants such as the isothiazolones. Price and Patchan (*Transactions of the institute of Marine Engineers*, pp. 1732-1742 (1991)) proposed delivering an antifouling agent using copper-coated lipid tubules or microcylinders.

Other traditional methods for encapsulation can be used. For example, the antifouling agent particles can be micro-coated, e.g., where the particles are coated with specially designed polymers in a fluidized bed reactor. The thickness of the coating material can be monitored and controlled by the dynamic operating conditions such as air flow, feed flow, temperature, nozzle size, substrate and the like. Another exemplary method is molecular inclusion wherein a hydrophobic antifouling agent is encapsulated within the "hydrophobic structure" of a host molecule such as beta-cyclodextrin. Another method of encapsulation is spray drying and coacervation of antifouling agents; this method enacapsulates the antifouling agent in a well-defined glassy matrix made of carbohydrates and polymers.

(ii) Additional Biocides

In various preferred embodiments, the antifouling agents of the present invention are incorporated into the coating compositions and coatings in combination with various other biocidal agents. For example, any of the metal chelates or metal salts described in (i) above may be combined with one or more additional biocides as described herein or otherwise known in the art.

One active ingredient effective for inhibiting fouling and sliming of submersed structures, as illustrated in Example 2, comprises copper (II) nitrate trihydrate, also known as cupric nitrate trihydrate, or copper dinitrate trihydrate. The copper (II) nitrate trihydrate may be used alone or in combination with other antifouling agents. For instance, the copper nitrate trihydrate may be used in combination with an organo-metallic biocide, an organic biocide, cuprous oxide, or other biocides. Non-limiting examples of organo-metallic biocides include zinc pyrithione, ZINEB, and copper naphthenate. Non-limiting examples of organic biocides include IRGAROL 1051 or SEANINE211. For the above combinations of copper (II) nitrate trihydrate and other biocidal agents, the ratio of antifouling agent to other biocidal agent(s) may be from about 1:100 to about 100:1; preferably, from about 1:10 to about 10:1; more preferably, from about 1:5 to about 5:1; even more preferably, from about 1:2 to about 2:1.

Additional preferred combinations of antifouling agent and other biocidal agents include compounds of formula (I), such as HMTBA-Cu and/or HMTBA-Zn, with a substituted 1,2-dihydroquinoline of formula (II):

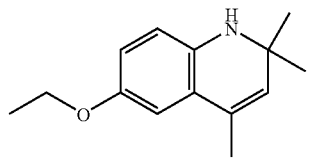

(II)

wherein:
$R^1$, $R^2$, $R^3$ and $R^4$ are independently selected from the group consisting of hydrogen and an alkyl group having from 1 to about 6 carbons; and
$R^5$ is an alkoxy group having from 1 to about 12 carbons.

In another embodiment, the substituted 1,2-dihydroquinoline will have formula (II)
wherein:
$R^1$, $R^2$, $R^3$ and $R^4$ are independently selected from the group consisting of hydrogen and an alkyl group having from 1 to about 4 carbons; and
$R^5$ is an alkoxy group having from 1 to about 4 carbons.

In a preferred embodiment, the substituted 1,2-dihydroquinoline will be 6-ethoxy-1,2-dihydro-2,2,4-trimethylquinoline having the structure:

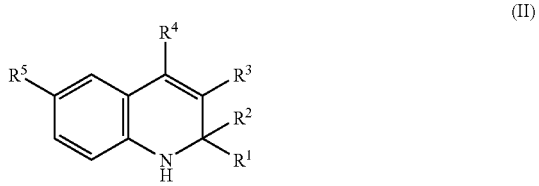

The compound 6-ethoxy-1,2-dihydro-2,2,4-trimethylquinoline, commonly known as ethoxyquin, is sold under the trademark SANTOQUIN®. The present invention also encompasses salts of ethoxyquin and other compounds having Formula (II). Ethoxyquin and other compounds having Formula (II) may be purchased commercially from Novus International, Inc. or made in accordance with methods generally known in the art, for example, as detailed in U.S. Pat. No. 4,772,710, which is hereby incorporated by reference in its entirety. In one preferred embodiment, HMTBA-Cu is used in combination with ethoxyquin. In another preferred embodiment, HMTBA-Zn is used in combination with ethoxyquin.

Other suitable biocidal agents can be, for example, copper isothiocyanate, N'-tert-butyl-N-cyclopropyl-6-(methylthio)-1,3,5-triazine-2,4-diamine (i.e., Irgarol 1051), N-dichlorofluoromethylthio-N',N'-dimethyl-N-phenylsulfamide (i.e., dichlofluanid), 3-(3,4-dichlorophenyl)-1,1-dimethylurea (i.e., diuron), 2-(thiocyanomethylthio) benzothiazole (i.e., TCMTB), tributyultin methacrylate copolymer (i.e., TBTM), tributyltin oxide (i.e., TBTO) and combinations thereof.

Suitable examples of combinations of antifouling agents are detailed in Table A.

TABLE A

| FIRST AGENT | ADDITIONAL AGENTS |
|---|---|
| Metal chelate of formula 1 or 1a | copper isothiocyanate |
| Metal chelate of formula 1 or 1a | N'-tert-butyl-N-cyclopropyl-6-(methylthio)-1,3,5-triazine-2,4-diamine (i.e., Irgarol 1051) |
| Metal chelate of formula 1 or 1a | N-dichlorofluoromethylthio-N',N'-dimethyl-N-phenylsulfamide (i.e., dichlofluanid) |
| Metal chelate of formula 1 or 1a | 3-(3,4-dichlorophenyl)-1,1-dimethylurea (i.e., diuron) |
| Metal chelate of formula 1 or 1a | 2-(thiocyanomethylthio) benzothiazole (i.e., TCMTB) |
| Metal chelate of formula 1 or 1a | tributyultin methacrylate copolymer (i.e., TBTM) |
| Metal chelate of formula 1 or 1a | tributyltin oxide (i.e., TBTO) |
| Metal chelate of formula 1 or 1a | N-dichlorofluoromethylthio-N',N'-dimethyl-N-phenylsulfamide |
| Metal chelate of formula 1 or 1a | 3-(3,4-dichlorophenyl)-1,1-dimethylurea |

TABLE A-continued

| FIRST AGENT | ADDITIONAL AGENTS |
| --- | --- |
| Metal chelate of formula 1 or 1a | copper isothiocyanate and N'-tert-butyl-N-cyclopropyl-6-(methylthio)-1,3,5-triazine-2,4-diamine |
| Metal chelate of formula 1 or 1a | copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide |
| Metal chelate of formula 1 or 1a | N'-tert-butyl-N-cyclopropyl-6-(methylthio)-1,3,5-triazine-2,4-diamine and 3-(3,4-dichlorophenyl)-1,1-dimethylurea |
| Metal chelate of formula 1 or 1a | N'-tert-butyl-N-cyclopropyl-6-(methylthio)-1,3,5-triazine-2,4-diamine and N-dichlorofluoromethylthio-N',N'-dimethyl-N-phenylsulfamide |
| Metal chelate of formula 1 or 1a | N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole |
| Metal chelate of formula 1 or 1a | tributyultin methacrylate copolymer and tributyltin oxide |
| Metal chelate of formula 1 or 1a | 1,2-dihydroquinoline |
| Metal chelate of formula 1 or 1a | 6-ethoxy-1,2-dihydro-2,2,4-trimethylquinoline |
| Metal salt of formula 1 or 1a | copper isothiocyanate |
| Metal salt of formula 1 or 1a | N'-tert-butyl-N-cyclopropyl-6-(methylthio)-1,3,5-triazine-2,4-diamine (i.e., Irgarol 1051) |
| Metal salt of formula 1 or 1a | N-dichlorofluoromethylthio-N',N'-dimethyl-N-phenylsulfamide (i.e., dichlofluanid) |
| Metal salt of formula 1 or 1a | 3-(3,4-dichlorophenyl)-1,1-dimethylurea (i.e., diuron) |
| Metal salt of formula 1 or 1a | 2-(thiocyanomethylthio) benzothiazole (i.e., TCMTB) |
| Metal salt of formula 1 or 1a | tributyultin methacrylate copolymer (i.e., TBTM) |
| Metal salt of formula 1 or 1a | tributyltin oxide (i.e., TBTO) |
| Metal salt of formula 1 or 1a | N-dichlorofluoromethylthio-N',N'-dimethyl-N-phenylsulfamide |
| Metal salt of formula 1 or 1a | 3-(3,4-dichlorophenyl)-1,1-dimethylurea |
| Metal salt of formula 1 or 1a | copper isothiocyanate and N'-tert-butyl-N-cyclopropyl-6-(methylthio)-1,3,5-triazine-2,4-diamine |
| Metal salt of formula 1 or 1a | copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide |
| Metal salt of formula 1 or 1a | N'-tert-butyl-N-cyclopropyl-6-(methylthio)-1,3,5-triazine-2,4-diamine and 3-(3,4-dichlorophenyl)-1,1-dimethylurea |
| Metal salt of formula 1 or 1a | N'-tert-butyl-N-cyclopropyl-6-(methylthio)-1,3,5-triazine-2,4-diamine and N-dichlorofluoromethylthio-N',N'-dimethyl-N-phenylsulfamide |
| Metal salt of formula 1 or 1a | N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole |
| Metal salt of formula 1 or 1a | tributyultin methacrylate copolymer and tributyltin oxide |
| Metal salt of formula 1 or 1a | 1,2-dihydroquinoline of formula 2 |
| Metal salt of formula 1 or 1a | 6-ethoxy-1,2-dihydro-2,2,4-trimethylquinoline |
| Metal chelate or salt of HMTBA | copper isothiocyanate |
| Metal chelate or salt of HMTBA | N'-tert-butyl-N-cyclopropyl-6-(methylthio)-1,3,5-triazine-2,4-diamine (i.e., Irgarol 1051) |
| Metal chelate or salt of HMTBA | N-dichlorofluoromethylthio-N',N'-dimethyl-N-phenylsulfamide (i.e., dichlofluanid) |
| Metal chelate or salt of HMTBA | 3-(3,4-dichlorophenyl)-1,1-dimethylurea (i.e., diuron) |
| Metal chelate or salt of HMTBA | 2-(thiocyanomethylthio) benzothiazole (i.e., TCMTB) |
| Metal chelate or salt of HMTBA | tributyultin methacrylate copolymer (i.e., TBTM) |
| Metal chelate or salt of HMTBA | tributyltin oxide (i.e., TBTO) |
| Metal chelate or salt of HMTBA | N-dichlorofluoromethylthio-N',N'-dimethyl-N-phenylsulfamide |
| Metal chelate or salt of HMTBA | 3-(3,4-dichlorophenyl)-1,1-dimethylurea |
| Metal chelate or salt of HMTBA | copper isothiocyanate and N'-tert-butyl-N-cyclopropyl-6-(methylthio)-1,3,5-triazine-2,4-diamine |
| Metal chelate or salt of HMTBA | copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide |

TABLE A-continued

| FIRST AGENT | ADDITIONAL AGENTS |
|---|---|
| Metal chelate or salt of HMTBA | N'-tert-butyl-N-cyclopropyl-6-(methylthio)-1,3,5-triazine-2,4-diamine and 3-(3,4-dichlorophenyl)-1,1-dimethylurea |
| Metal chelate or salt of HMTBA | N'-tert-butyl-N-cyclopropyl-6-(methylthio)-1,3,5-triazine-2,4-diamine and N-dichlorofluoromethylthio-N',N'-dimethyl-N-phenylsulfamide |
| Metal chelate or salt of HMTBA | N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole |
| Metal chelate or salt of HMTBA | tributyultin methacrylate copolymer and tributyltin oxide |
| Metal chelate or salt of HMTBA | 1,2-dihydroquinoline or formula 2 |
| Metal chelate or salt of HMTBA | 6-ethoxy-1,2-dihydro-2,2,4-trimethylquinoline |
| HMTBA-Zn | copper isothiocyanate |
| HMTBA-Zn | N'-tert-butyl-N-cyclopropyl-6-(methylthio)-1,3,5-triazine-2,4-diamine (i.e., Irgarol 1051) |
| HMTBA-Zn | N-dichlorofluoromethylthio-N',N'-dimethyl-N-phenylsulfamide (i.e., dichlofluanid) |
| HMTBA-Zn | 3-(3,4-dichlorophenyl)-1,1-dimethylurea (i.e., diuron) |
| HMTBA-Zn | 2-(thiocyanomethylthio) benzothiazole (i.e., TCMTB) |
| HMTBA-Zn | tributyultin methacrylate copolymer (i.e., TBTM) |
| HMTBA-Zn | tributyltin oxide (i.e., TBTO) |
| HMTBA-Zn | N-dichlorofluoromethylthio-N',N'-dimethyl-N-phenylsulfamide |
| HMTBA-Zn | 3-(3,4-dichlorophenyl)-1,1-dimethylurea |
| HMTBA-Zn | copper isothiocyanate and N'-tert-butyl-N-cyclopropyl-6-(methylthio)-1,3,5-triazine-2,4-diamine |
| HMTBA-Zn | copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide |
| HMTBA-Zn | N'-tert-butyl-N-cyclopropyl-6-(methylthio)-1,3,5-triazine-2,4-diamine and 3-(3,4-dichlorophenyl)-1,1-dimethylurea |
| HMTBA-Zn | N'-tert-butyl-N-cyclopropyl-6-(methylthio)-1,3,5-triazine-2,4-diamine and N-dichlorofluoromethylthio-N',N'-dimethyl-N-phenylsulfamide |
| HMTBA-Zn | N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole |
| HMTBA-Zn | tributyultin methacrylate copolymer and tributyltin oxide |
| HMTBA-Zn | 1,2-dihydroquinoline of formula 2 |
| HMTBA-Zn | 6-ethoxy-1,2-dihydro-2,2,4-trimethylquinoline |
| HMTBA-Cu | copper isothiocyanate |
| HMTBA-Cu | N'-tert-butyl-N-cyclopropyl-6-(methylthio)-1,3,5-triazine-2,4-diamine (i.e., Irgarol 1051) |
| HMTBA-Cu | N-dichlorofluoromethylthio-N',N'-dimethyl-N-phenylsulfamide (i.e., dichlofluanid) |
| HMTBA-Cu | 3-(3,4-dichlorophenyl)-1,1-dimethylurea (i.e., diuron) |
| HMTBA-Cu | 2-(thiocyanomethylthio) benzothiazole (i.e., TCMTB) |
| HMTBA-Cu | tributyultin methacrylate copolymer (i.e., TBTM) |
| HMTBA-Cu | tributyltin oxide (i.e., TBTO) |
| HMTBA-Cu | N-dichlorofluoromethylthio-N',N'-dimethyl-N-phenylsulfamide |
| HMTBA-Cu | 3-(3,4-dichlorophenyl)-1,1-dimethylurea |
| HMTBA-Cu | copper isothiocyanate and N'-tert-butyl-N-cyclopropyl-6-(methylthio)-1,3,5-triazine-2,4-diamine |
| HMTBA-Cu | copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide |
| HMTBA-Cu | N'-tert-butyl-N-cyclopropyl-6-(methylthio)-1,3,5-triazine-2,4-diamine and 3-(3,4-dichlorophenyl)-1,1-dimethylurea |
| HMTBA-Cu | N'-tert-butyl-N-cyclopropyl-6-(methylthio)-1,3,5-triazine-2,4-diamine and N-dichlorofluoromethylthio-N',N'-dimethyl-N-phenylsulfamide |

TABLE A-continued

| FIRST AGENT | ADDITIONAL AGENTS |
|---|---|
| HMTBA-Cu | N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole |
| HMTBA-Cu | tributyultin methacrylate copolymer and tributyltin oxide |
| HMTBA-Cu | 1,2-dihydroquinoline of formula 2 |
| HMTBA-Cu | 6-ethoxy-1,2-dihydro-2,2,4-trimethylquinoline |
| Copper (II) nitrate trihydrate | copper isothiocyanate |
| Copper (II) nitrate trihydrate | N'-tert-butyl-N-cyclopropyl-6-(methylthio)-1,3,5-triazine-2,4-diamine (i.e., Irgarol 1051) |
| Copper (II) nitrate trihydrate | N-dichlorofluoromethylthio-N',N'-dimethyl-N-phenylsulfamide (i.e., dichlofluanid) |
| Copper (II) nitrate trihydrate | 3-(3,4-dichlorophenyl)-1,1-dimethylurea (i.e., diuron) |
| Copper (II) nitrate trihydrate | 2-(thiocyanomethylthio) benzothiazole (i.e., TCMTB) |
| Copper (II) nitrate trihydrate | tributyultin methacrylate copolymer (i.e., TBTM) |
| Copper (II) nitrate trihydrate | tributyltin oxide (i.e., TBTO) |
| Copper (II) nitrate trihydrate | N-dichlorofluoromethylthio-N',N'-dimethyl-N-phenylsulfamide |
| Copper (II) nitrate trihydrate | 3-(3,4-dichlorophenyl)-1,1-dimethylurea |
| Copper (II) nitrate trihydrate | copper isothiocyanate and N'-tert-butyl-N-cyclopropyl-6-(methylthio)-1,3,5-triazine-2,4-diamine |
| Copper (II) nitrate trihydrate | copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide |
| Copper (II) nitrate trihydrate | N'-tert-butyl-N-cyclopropyl-6-(methylthio)-1,3,5-triazine-2,4-diamine and 3-(3,4-dichlorophenyl)-1,1-dimethylurea |
| Copper (II) nitrate trihydrate | N'-tert-butyl-N-cyclopropyl-6-(methylthio)-1,3,5-triazine-2,4-diamine and N-dichlorofluoromethylthio-N',N'-dimethyl-N-phenylsulfamide |
| Copper (II) nitrate trihydrate | N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole |
| Copper (II) nitrate trihydrate | tributyultin methacrylate copolymer and tributyltin oxide |
| Copper (II) nitrate trihydrate | 1,2-dihydroquinoline of formula 2 |
| Copper (II) nitrate trihydrate | 6-ethoxy-1,2-dihydro-2,2,4-trimethylquinoline |
| Copper (II) nitrate trihydrate | Organic biocide |
| Copper (II) nitrate trihydrate | Organo-metallic biocide |
| Copper (II) nitrate trihydrate | Cuprous oxide |
| Copper (II) nitrate trihydrate | Zinc pyrithione |
| Copper (II) nitrate trihydrate | ZINEB |
| Copper (II) nitrate trihydrate | Copper naphthenate |
| Copper (II) nitrate trihydrate | SEANINE211 |
| Zinc | Alanine or its hydroxy analog |
| Zinc | Arginine or its hydroxy analog |
| Zinc | Asparagine or its hydroxy analog |
| Zinc | Aspartic acid or its hydroxy analog |
| Zinc | Cysteine or its hydroxy analog |
| Zinc | Glutamine or its hydroxy analog |
| Zinc | Glutamic acid or its hydroxy analog |
| Zinc | Glycine or its hydroxy analog |
| Zinc | Histidine or its hydroxy analog |
| Zinc | Isoleucine or its hydroxy analog |
| Zinc | Leucine or its hydroxy analog |
| Zinc | Lysine or its hydroxy analog |
| Zinc | Methionine or its hydroxy analog |
| Zinc | Phenylalanine or its hydroxy analog |
| Zinc | Proline or its hydroxy analog |
| Zinc | Serine or its hydroxy analog |
| Zinc | Threonine or its hydroxy analog |
| Zinc | Tryptophan or its hydroxy analog |
| Zinc | Tyrosine or its hydroxy analog |
| Zinc | Valine or its hydroxy analog |
| Copper | Alanine or its hydroxy analog |
| Copper | Arginine or its hydroxy analog |
| Copper | Asparagine or its hydroxy analog |
| Copper | Aspartic acid or its hydroxy analog |
| Copper | Cysteine or its hydroxy analog |
| Copper | Glutamine or its hydroxy analog |
| Copper | Glutamic acid or its hydroxy analog |

TABLE A-continued

| FIRST AGENT | ADDITIONAL AGENTS |
| --- | --- |
| Copper | Glycine or its hydroxy analog |
| Copper | Histidine or its hydroxy analog |
| Copper | Isoleucine or its hydroxy analog |
| Copper | Leucine or its hydroxy analog |
| Copper | Lysine or its hydroxy analog |
| Copper | Methionine or its hydroxy analog |
| Copper | Phenylalanine or its hydroxy analog |
| Copper | Proline or its hydroxy analog |
| Copper | Serine or its hydroxy analog |
| Copper | Threonine or its hydroxy analog |
| Copper | Tryptophan or its hydroxy analog |
| Copper | Tyrosine or its hydroxy analog |
| Copper | Valine or its hydroxy analog |

In various preferred embodiments, the antifouling agent in combination with other biocidal agents is selected from HMTBA-Zn, HMTBA-Cu and combinations thereof. Preferably, the antifouling agent in combination with other biocidal agents comprises HMTBA-Zn. Alternatively, the antifouling agent in combination with other biocidal agents comprises HMTBA-Cu. In many embodiments, the total concentration of the combination of antifouling agent and other biocidal agent or agents as described above can be from about 0.05 wt. % to about 50 wt. % in the coating compositions; preferably, from about 0.1 wt. % to about 25 wt. %; more preferably, from about 1 wt. % to about 10 wt. %. Analogously, the total concentration of the combination of antifouling agent and other biocidal agent or agents in the coating can be from about 0.07 wt. % to about 72 wt. %; preferably, from about 0.15 wt. % to about 36 wt. %; more preferably, from about 1 wt. % to about 14 wt. %.

Preferred combinations of antifouling agent and other biocidal agent or agents are (1) HMTBA-Zn and/or HMTBA-Cu with copper isothiocyanate; (2) HMTBA-Zn and/or HMTBA-Cu with N'-tert-butyl-N-cyclopropyl-6-(methylthio)-1,3,5-triazine-2,4-diamine; (3) HMTBA-Zn and/or HMTBA-Cu with N-dichlorofluoromethylthio-N',N'-dimethyl-N-phenylsulfamide; (4) HMTBA-Zn and/or HMTBA-Cu with 3-(3,4-dichlorophenyl)-1,1-dimethylurea; (5) HMTBA-Zn and/or HMTBA-Cu with copper isothiocyanate and N'-tert-butyl-N-cyclopropyl-6-(methylthio)-1,3,5-triazine-2,4-diamine; (6) HMTBA-Zn and/or HMTBA-Cu with copper isothiocyanate, N'-tert-butyl-N-cyclopropyl-6-(methylthio)-1,3,5-triazine-2,4-diamine and N-dichlorofluoromethylthio-N',N'-dimethyl-N-phenylsulfamide; (7) HMTBA-Zn and/or HMTBA-Cu with N'-tert-butyl-N-cyclopropyl-6-(methylthio)-1,3,5-triazine-2,4-diamine and 3-(3,4-dichlorophenyl)-1,1-dimethylurea; (8) HMTBA-Zn and/or HMTBA-Cu with N'-tert-butyl-N-cyclopropyl-6-(methylthio)-1,3,5-triazine-2,4-diamine and N-dichlorofluoromethylthio-N', N'-dimethyl-N-phenylsulfamide; (9) HMTBA-Zn and/or HMTBA-Cu with N'-tert-butyl-N-cyclopropyl-6-(methylthio)-1,3,5-triazine-2,4-diamine, 3-(3,4-dichlorophenyl)-1,1-dimethylurea and 2-(thiocyanomethylthio) benzothiazole; and (10) HMTBA-Zn and/or HMTBA-Cu with tributyultin methacrylate copolymer and tributyltin oxide.

For the above combinations of antifouling agents and other biocidal agents, the ratio of antifouling agent to other biocidal agent(s) is from about 1:100 to about 100:1; preferably, from about 1:10 to about 10:1; more preferably, from about 1:5 to about 5:1; even more preferably, from about 1:2 to about 2:1.

In various preferred embodiments the ratio of antifouling agent or agents to other biocidal agent(s) is about 1:2. Thus, from the ratio above, the concentration range of the antifouling agent in a coating composition including other biocidal agent(s) is from about 0.015 wt. % to about 17 wt. %; preferably, from about 0.03 wt. % to about 9 wt. %; more preferably, from about 0.3 wt. % to about 3 wt. %. In other preferred embodiments, the concentration range of the antifouling agent in a coating including other biocidal agent(s) is from about 0.02 wt. % to about 24 wt. %; preferably, from about 0.04 wt. % to about 13 wt. %; more preferably, from about 0.4 wt. % to about 4 wt. %. Further, the concentration range of the other biocidal agents is from about 0.035 wt. % to about to about 33 wt. %; preferably, from about 0.07 wt. % to about 16 wt. %; more preferably, from about 0.7 wt. % to about 7 wt. %. In other preferred embodiments, the concentration range of the antifouling agent in a coating including other biocidal agent(s) is from about 0.05 wt. % to about 47 wt. %; preferably, from about 0.1 wt. % to about 23 wt. %; more preferably, from about 1 wt. % to about 10 wt. %.

B. Organic Vehicles

The marine coatings and marine coating compositions of the present invention comprise an organic vehicle. The organic vehicle is selected from the group consisting of resins, organic diluents and combinations thereof. Various preferred embodiments of the marine coatings contain a resin. In preferred embodiments of marine coating compositions, the organic vehicle comprises a resin and a diluent. Suitable resins and diluents are discussed in more detail below.

(i) Resins

As described above, there are at least three general mechanisms of release of antifouling agents from marine coatings. Self-polishing marine coatings contain resins that are self-polishing copolymers (SPC). An exemplary SPC coating contains a polymeric resin that contains triorganotin moieties as pendent groups. In this case, the triorganotin moieties are effective antifouling agents. Once the triorganotin moieties are hydrolyzed, they become soluble in seawater, so that as the outermost coating layer becomes depleted of antifouling agent, the outermost layer is swept off the surface of the hull by the movement of the ship through seawater. Thus, a fresh coating layer containing additional antifouling agent is exposed. Alternatives to triorganotin-based coatings are desired because of the undesirable environmental effects of these antifouling agents. Such alternatives may typically contain pendent groups attached to a polymer backbone that hydrolyze analogously to triorganotin moieties. The identity and number of pendent groups on the polymer backbone affects the hydrolysis rate of the resin. Self-polishing systems based on copper or zinc acrylates are also produced. Copper acrylate breaks down through hydrolysis reactions in a similar fashion to zinc methacrylate, but the zinc breaks down through an ion exchange mechanism, in which the zinc ions are replaced by sodium from seawater rendering the polymer more hydrophilic, and thus, solubilizing it, while chlorine anion from seawater salt bonds with the organo-zinc moiety.

Exemplary self-polishing copolymers are acrylic resins (e.g., polyester acrylic resins, epoxy acrylic resins, polyether acrylic resins, vinyl acrylic resins, styrene/acrylic copolymer resins, urethane acrylic resins, fluoroalkyl (meth)acrylate/silyl (meth)acrylate/alkyl (meth)acrylate terpolymers (e.g., as described in U.S. Pat. No. 6,767,978, expressly incorporated herein by reference) acrylic emulsion resins and polyol acrylic resins), copolymers of vinyl chloride, vinyl isobutyl ether, carboxylic acid functional polymers and combinations thereof. For example, a carboxylic acid function polymer can be a co-polymer of acrylic or methacrylic acid with one or more alkyl acrylate or methacrylate groups, wherein one or more of the acid groups have been converted to groups of the formula —COO—M—OH, where M is a divalent metal such as copper, zinc, calcium, magnesium or iron. The acrylate and methacrylate groups can be selected from the group consisting of acrylates and methacrylates (e.g., methyl (meth)acrylate, ethyl (methyl)acrylate, 1-propyl (meth)acrylate, 2-propyl (meth)acrylate, 1-butyl (meth) acrylate, 2-butyl (meth)acrylate, iso-butyl (meth)acrylate, and tert-butyl (meth)acrylate), cycloalkyl (meth)acrylate (e.g., cyclohexyl (meth)acrylate), haloalkyl (meth)acrylates (e.g., 2-chloroethyl (meth)acrylate), hydroxy-$C_{1-10}$-alkyl (meth)acrylates (e.g., 2-hydroxyethyl (meth)acrylate, 1-hydroxy-2-propyl (meth)acrylate, and 2-hydroxy-1-propyl (meth)acrylate), alkoxyalkyl (meth)acrylates (e.g., methoxyethyl (meth)acrylate and ethoxyethyl (meth)acrylate), benzyl (meth)acrylates and substituted analogues thereof (e.g., analogues substituted one, two, or three time on the benzene ring with $C_{1-7}$ alkyl, $C_{1-7}$ alkoxy, hydroxy, thio, cyano, nitro, or halogen), polyoxy-$C_{1-5}$ alkylene (meth) acrylate (e.g., polyoxyethylene (meth)acrylate and polyoxypropylene (meth)acrylate) and styrenes (e.g., styrene and α-methylstyrene, optionally substituted in the 2-, 3- or 4-position with $C_{1-7}$ alkyl, $C_{1-7}$ alkenyloxy, $C_{1-7}$ alkoxy, hydroxy, thio, cyano, nitro or halogen). Among preferred copolymers are vinyl ethers such as vinyl methyl ether, vinyl ethyl ether, vinyl propyl ether, vinyl ethylbutyl ether, vinyl hexyl ether, vinyl 2-ethylhexyl ether, and vinyl cyclohexyl ether. Vinyl chloride and vinyl isobutyl ether are those sold by BASF under the trade name Laroflex®. In preferred embodiments, the SPC marine coatings and compositions also contain rosin.

Preferably, in SPC-type marine coating compositions of the invention, the one or more self-polishing copolymers are included in the composition at a concentration of from about 3 wt. % to about 25 wt. %; preferably, about 5 wt. % to about 20 wt. %; more preferably, about 8 wt. % to about 16 wt. %; even more preferably, about 10 wt. % to about 14 wt. %. In preferred embodiments of the marine coatings of the invention, the one or more self-polishing copolymers are included in the dried and/or cured coating at a concentration of from about 4 wt. % to about 36 wt. %; preferably, about 7 wt. % to about 29 wt. %; more preferably, about 11 wt. % to about 23 wt. %; even more preferably, about 14 wt. % to about 20 wt. %.

Ablative coatings contain resins that are soluble in water to the extent that the coating is gradually washed away through contact of the coated structure with water. The rate at which the coating is dissolved is controlled and depends on the solubility of the resin. Exemplary ablative resins are selected from the group consisting of vinyl resins, alkyd resins, epoxy resins, acrylic resins, polyurethane resins, polyester resins, vinyl acrylic resins, vinyl esters (e.g., vinyl esters of $C_{2-20}$ linear or branched alkanoic, alkenoic, alkyldienoic acids) and combinations thereof. The function of ablative coatings is comparable to self-polishing polymers, except that the rate of removal of ablative coatings is regulated by the characteristics of the intact polymer, including its balance of hydrophilic and hydrophobic properties, rather than by progressive hydrolysis of linkages between the polymer and relatively hydrophobic pendent groups.

Preferably, in ablative marine coating compositions of the present invention, one or more ablative resins are present in the compositions at a concentration from about 10 wt. % to about 45 wt. %; from about 15 wt. % to about 40 wt. %; preferably, from about 18 wt. % to about 35 wt. %; more preferably, from about 21 wt. % to about 28 wt. %. In preferred embodiments of the dried and/or cured marine coatings of the invention, the one or more ablative resins are present in the coatings at a concentration of from about 14 wt. % to about 65 wt. %; from about 21 wt. % to about 57 wt. %; preferably, from about 25 wt. % to about 50 wt. %; more preferably, from about 30 wt. % to about 40 wt. %.

Leaching coatings are porous and comprise a matrix composed of both water-resistant and water-soluble or water-dispersible resins. As the water-dispersible components are contacted and progressively removed by contact with water absorbed into the pores, the coating develops a honeycomb structure that is permeable to seawater, but retains the mechanical properties of hardness and resistance to removal. As a result of contact of seawater (or fresh water) with the antifouling agents contained within the honeycomb coating, attachment of marine organisms is inhibited.

Preferably, in leaching marine coating compositions of the present invention, one or more leaching resins are present in the compositions at a concentration from about 10 wt. % to about 45 wt. %; preferably, from about 15 wt. % to about 40 wt. %; more preferably, from about 18 wt. % to about 35 wt. %. In preferred embodiments of the dried and/or cured marine coatings of the invention, the one or more leaching resins are present in the coatings at a concentration from about 14 wt. % to about 64 wt. %; preferably, from about 21 wt. % to about 57 wt. %; more preferably, from about 25 wt. % to about 50 wt. %.

The resins of the organic vehicle may also comprise rosins. For example, suitable rosins are selected from the group consisting of gum rosin, wood rosin of grades B, C, D, E, F, FF, G, H, I, J, K, L, M, N, W-G, W-W (as defined by the ASTM D509 standard), virgin rosin, hard rosin, yellow dip rosin, NF wood rosin, tail oil rosin, colophony, colophonium, single constituents of natural rosin (e.g., abietic acid, abietinic acid, sylvic acid, dihydroabietic acid, tetrahydroabietic acid, dehydroabietic acid, neoabietic acid, pimaric acid, laevopimaric acid, isopimaric acid, sandaracopimaric acid, palustric acid, dextro-pimaric acid, isodextro-pimaric acid, dextro-pimarinal, isodextro-pimarinal, xanthoperol, tatarol, podocarpic acid, phyllocladen, sugiol, ferruginol, himokiol, manool, manoyloxide, ketomanoyloxide, cativinic acid, eperuanic acid and all other rosin components based on the diterpene skeleton of abietic acid) and combinations thereof.

In various preferred embodiments, the marine coating composition comprises a self-polishing copolymer or resin that yield a coating that is ablative.

The marine coatings described above are designed to regulate the leaching of antifouling agents by a controlled, and preferably uniform, release of the agents through the entire coating lifetime. The lifetime of marine coatings is typically 2-5 years, and preferably 5-10 years or longer. The optimal design and performance of marine coatings depends on several variables associated with the ship profile and sailing pattern. Temperature, fouling intensity, salinity, dry-docking intervals, vessel speed, and antifouling activity are the main factors that influence the coating behavior. Thus, with the appropriate selection of components from those described above, one skilled in the art can tailor make marine coating compositions that yield coatings having leaching rates in a wide range, so that the coatings are applicable for a number of different vessel types.

Normally a ship operating at low speed with very low activity in an area of a high fouling intensity, e.g. a container ship sailing on Singapore, will need a relatively fast leaching coating, e.g., a coating which releases the aforesaid antifouling agent at a rate of about 1 to about 10 μg antifouling agent/d per cm$^2$ of submerged ship hull surface. Typically a self-polishing or ablative coating may degrade at a rate in the range of 10-30 μm per 10,000 Nautical miles, in order to release sufficient amounts of antifouling agents to keep the hull clean. On the other hand a ship operating at high speed with very high activity in an area of a low to moderate fouling intensity, e.g. coastal fishing vessels in Iceland, will need a relatively slow leaching coating, e.g. having a rate of coating degradation in the range of 1-3 μm per 10,000 Nautical miles.

The marine coating compositions of the present invention are usually formulated and used in the form of paint compositions. However, they may be formulated and used in other forms (such as solutions or emulsifiable concentrates) as the case requires. Paint vehicles to be used for formulating the compounds of the present invention into coating compositions, may include other resins in additional to those described above. For example, a vinyl chloride resin, a vinyl chloride-vinyl acetate copolymer, a vinyl chloride-vinyl isobutyl ether copolymer, a chlorinated rubber resin, a chlorinated polyethylene resin, a chlorinated polypropylene resin, an acrylic resin, a styrene-butadiene resin, a polyester resin, an epoxy resin, a phenol resin, a synthetic rubber, a silicone rubber, a silicone resin, a petroleum resin, an oil and fat resin, a rosin ester resin, a rosin soap or rosin may be used.

(ii) Diluents

In various embodiments, the marine coating compositions also contain a diluent. The diluent is selected from the group consisting of alcohols, aliphatic, cycloaliphatic and aromatic hydrocarbons, ketones, ether alcohols, esters, chlorinated hydrocarbons and combinations thereof. Typically, the diluent may function as a solvent for the antifouling agent and/or for a resin component of the composition. Preferably, the diluent is selected from the group consisting of methanol, ethanol, propanol, isopropanol, butanol, isobutanol, benzyl alcohol, white spirit, cyclohexane, toluene, xylene, methyl ethyl ketone, acetone, methyl isobutyl ketone, methyl isoamyl ketone, diacetone alcohol, cyclo-hexanone, 2-butoxyethanol, propylene glycol monomethyl ether, butyl diglycol, methoxypropyl acetate, n-butyl acetate, 2-ethoxyethyl acetate, methylene chloride, tetrachloroethane, trichloroethylene and combinations thereof.

Preferably, the diluent is present in the marine coating compositions in a concentration from about 5 wt. % to about 50 wt. %; preferably, from about 20 wt. % to about 45 wt. %; more preferably, from about 20 wt. % to about 30 wt. %.

In the marine coatings of the present invention, typically, the diluent evaporates once the coating composition is applied to the marine structure. Therefore, the dried and/or cured marine coatings have a minimal concentration of diluents in the coating.

C. Additives

In general, additives may be contained in the marine coating compositions and marine coatings. Additives may be selected from the group consisting of pigments, fillers, extenders, swelling agents, wetting agents, biocides and combinations thereof. Pigments, for example, can be organic or inorganic pigments. Typical pigments for use in marine coatings are selected from the group consisting of phthalo blue, hansa yellow, ochres, umbers, Quinacridone Red, Pigment Red, Phthalocyanine Blue, Phthalocyanine Green, Perylene Red, carbon black, rutile and anatase titanium dioxides, lithopone, zinc sulfide, lead titanate, antimony oxide, zirconium oxide, barium sulfide, white lead, zinc oxide, leaded zinc oxide, red iron oxide, brown oxide, aluminium powder, vapor-deposited aluminium powder, alumina powder, nickel powder, copper powder, brass powder, chromium powder, nacreous pearl mica powder and nacreous colored pearl mica powder and combinations thereof.

Pigments may be present in the marine coating compositions in concentrations from about 1 wt. % to about 50 wt. %; preferably, from about 10 wt. % to about 40 wt. %; more preferably, from about 15 wt. % to about 35 wt. %. Dried and/or cured marine coatings of the present invention may contain pigments in concentrations from about 1 wt. % to about 72 wt. %; preferably, from about 14 wt. % to about 57 wt. %; more preferably, from about 21 wt. % to about 50 wt. %.

Fillers are materials that usually have a fine particle size, are dispersable in organic media and do not settle once dispersed. Exemplary fillers are selected from the group consisting of calcium carbonate, iron oxide, kaolin, clay, titanium dioxide, alumina trihydrate, pyrophyllite, quartz, silica, fumed silicas, precipitated silicas, silicates, barium sulfate, antimony oxide, mica, calcium sulfate, magnesium hydroxide, feldspar, nepheline syenite, carbon black filler, titanates, talc, gypsum, silex, wollastonite, bagasse, coconut hull/fiber, cork, corn, cotton-based, filsonite, nutshell flour, rice hull, sisal/hemp, soybean, starch wood flour and combinations thereof.

Fillers may be present in the marine coating compositions in concentrations from about 1 wt. % to about 35 wt. %; preferably, from about 2 wt. % to about 22 wt. %; more preferably, from about 2 wt. % to about 5 wt. %. Dried and/or cured marine coatings of the present invention may contain fillers in concentrations from about 1 wt. % to about 50 wt. %; preferably, from about 3 wt. % to about 32 wt. %; more preferably, from about 3 wt. % to about 7 wt. %.

Swelling agents are compounds that increase in volume when in contact with a liquid. Preferably, swelling agents are included in the ablative marine coating compositions because the presence of the swelling agent aids the coating degradation by helping the coating to "slough off" upon contact with water. Suitable swelling agents are selected from the group consisting of modified bentonite, kaoline, montomorillonite bentonite, clay mica (muscovite), cholorite (hectonite), non-alkaline magnesia alumosilicate, quartz, silica, high silica, soda silicate, magnesia alumosilicate, soda borosilicate, polycarbonsilane, polytitanocarbosilane, polysilazane, tobermorite, samarium silicate, wollastonite, potassium aluminium silicate, hydroxyapatite, calcium hydrogenphosphate, neodymium pentaphosphate, silver phosphate, calcium sulfate, calcium iodate, phlogopite, biotite, sodium aluminium hydroxycarbonate, rockwool, basalt rockwool, processed mineral fibers, volcanic rock, atapulgite, calcined bauxite and combinations thereof. In preferred embodiments, the marine coating and the dried and/or cured marine coating composition comprise a modified bentonite available from NL Chemicals under the trade name Bentone SD®. Typically, swelling agents are present in the marine coating compositions at concentrations up to about 5 wt. %; preferably, from about 0.1 wt. % to about 3 wt. %; more preferably, from about 0.5 wt. % to about 2 wt. %.

Wetting agents are substances that reduce the surface tension of a liquid and cause the liquid to spread across or penetrate more easily the surface of a solid. Exemplary wetting agents are selected from the group consisting of a solution of a salt of unsaturated polyamine amides and lower molecular acid polymers, sodium polyphosphate, aryl or alkyl phosphates, salts of low molecular weight poly(acrylic acid), salts of sulfonated polyethylene, salts of poly (vinylphosphonic acid), salts of poly(maleic acid), salts of copolymers of maleic acid with olefins, and combinations thereof. In preferred embodiments, the dried and/or cured marine coating and the marine coating composition comprise a solution of a salt of unsaturated polyamine amides and lower molecular acid polymers sold by BYK Chemie under the trade name Anti-Terra®-U. In addition to its function as a wetting agent Anti-Terra®-U acts as a dispersing agent by deflocculating pigments. It stabilizes the pigments through steric interaction and balances the electric charge of pigments.

The marine coating compositions containing the metal chelate or metal salt antifouling agent of the present invention may further contain other known inorganic or organic antifouling agents, as the case requires. Such an antifouling agent includes, for example, cuprous oxide, copper rhodanide, copper hydroxide, copper nitrate, copper (II) nitrate trihydrate, copper naphthenate, metallic copper and various tin compounds and dithiocarbamic acid derivatives, such as tetramethylthiuram monosulfide, tetramethylthiuram disulfide, zinc bis-(dimethyldithiocarbamate), zinc ethylene-bis(dithiocarbamate), manganese ethylene-bis(dithiocarbamate), and copper bis(dimethyldithiocarbamate) and combinations thereof.

Typically, a marine coating composition includes organic vehicles such as resins and diluents and additives as described above. Preferred formulations for ablative and self-polishing copolymer (SPC) marine coating compositions are presented in Table 1 below.

TABLE 1

MARINE PAINT COMPOSITIONS

ABLATIVE

| CU | Material | PERCENT |
|---|---|---|
| Acros Organics | Cuprous Oxide | 35.0-45.0 |
| Aldrich | Zinc Oxide | 8.0-15.0 |
| Bayer | Iron oxide (filler) | 1.5-3.0 |
| NL Chemicals | Bentone ® SD | 0.5-1.2 |
| Rohm & Haas | Metamare ® B175 | 18.0-25.0 |

TABLE 1-continued

MARINE PAINT COMPOSITIONS

| Byk Chemie | Antitera ®-U | 0.5-01.5 |
|---|---|---|
| Aldrich | Mixed Solvent | 20-3 |

ALBLATIVE

| Metal Free | Material | PERCENT |
|---|---|---|
| Aldrich | Cuprous Oxide | 0.00 |
|  | Zinc Oxide | 35.0-50.0 |
| NL Chemicals | Bentone ® SD | 0.5-2.0 |
| Rohm & Haas | Metamare ® B175 | 20.0-35.0 |
| Byk Chemie | Antitera ®-U | 0.4-0.9 |
| Aldrich | Mixed Solvent | 30.0-45.0 |

SPC TYPE

| copper | Material | PERCENT |
|---|---|---|
| Brand NU Labs | Cuprous Oxide | 35.0-45.0 |
| Aldrich | Zinc Oxide | 8.0-12.5 |
| Bayer | Iron oxide (filler) | 2.5-5.0 |
| Aldrich | Rosin | 8.0-15.0 |
|  | Acrylic Resin | 5.0-10.0 |
| BASF | Ext. Resin (Laroflex ® type) | 3.0-6.0 |
| Aldrich | Mixed Solvent | 20.0-30.0 |

SPC TYPE

| Metal Free | Material | PERCENT |
|---|---|---|
| Aldrich | Cuprous Oxide | 0.00 |
|  | Zinc Oxide | 1.0-3.5 |
| Bayer | Iron oxide (filler) | 15.0-28.0 |
| Aldrich | Rosin | 5.0-15.0 |
|  | Acrylic Resin | 5.0-15.0 |
| BASF | Ext. Resin (Laroflex ® type) | 3.0-8.0 |
| Aldrich | Mixed Solvent | 40.0-50.0 |

D. Preparation of Marine Coatings

The marine coating compositions described above in Table 1 were prepared by adding the wetting agent (e.g., Antiterra®-U) to the polymer resin (not including the wood rosin) solution dissolved in a solvent mixture including tricresyl phosphate. This mixture was mixed with a high speed dispenser at 1,000 rpm for 5 minutes. Then, the metal oxide(s) and bentone were added slowly with mixing. Once addition of the ingredients was complete, mixing was continued at 3,000 rpm for 35 minutes. The temperature was maintained below 45° C. using a water bath. The particle size of the solids contained in the composition was determined and during the letdown stage, a solution of wood rosin in a solvent mixture and the remaining solvent was added to the container with mixing for 15 minutes at 2,000 rpm. The letdown stage is the stage where additional solvents are added after grinding is completed. Typically, less than the total volume of solvent is added to the mixture in the initial high speed mixing stage because it is difficult and inefficient to mix the solid components with excess solvent present.

When the antifouling agent is a powder, the particle size may need to be reduced prior to incorporation into the coating composition. For example, in various embodiments, HMTBA-Zn has a mean particle size of about 450 μm and HMTBA-Cu has a mean particle size of about 350 μm. The particle size of these antifouling agents is desirably reduced to produce satisfactory dispersion in the paints. Thus, the antifouling agent particles can be ground to break up the larger particles. Particularly, the powdered antifouling agents could be jet milled to the desired particle size as described above.

The marine coating compositions of the present invention can be prepared by using e.g. a ball mill, a pebble mill, a roll mill or a sand grinder in accordance with methods well known in the field. Further, the above marine coating compositions may contain a plasticizer, a coloring pigment, an extender pigment, an organic solvent, and the like, which are commonly used in this field.

The marine coating compositions of the present invention may be used as part of a coating system that includes surface primer, filler and primer in addition to a marine coating composition comprising an antifouling agent. As known by those skilled in the art, a series of primers and a filler may be necessary or desirable depending on the condition of the marine structure to be coated. For example, if the surface condition is rough and/or it has many dents, a primer followed by a filler and sanding may be necessary before applying another compatible primer followed by a top coat of the marine coating composition. In addition, depending on the material to be coated, the sequence of application steps and selection of appropriate coating compositions is within the knowledge in the art.

For instance, the primer can be of the following types: (1) phenolic/polyvinyl butyral (PVB), acid cured, one- and two-pack compositions; (2) two pack cold curing epoxy compositions; and (3) zinc silicate one- and two-pack compositions. A one-pack composition is a primer composition wherein the film former is present in the composition. A two-pack composition is a primer composition where there are two film forming components that come in separate containers and are combined in order to prepare the primer composition. The filler composition is selected to be compatible with the substrate material that is being coated.

Generally, for marine structural elements made of steel, fiberglass and plastic, the SPC and ablative marine coatings described above could be used to coat the structure above and below the water line. Where the marine structural element is made of steel, the first coat of the marine coating is applied to a near white sand-blasted steel surface. Preferably, the marine coating compositions are applied to the submersible portions of the marine structural element. The antifouling agents are preferably distributed uniformly throughout the composition as it is applied to a marine underwater structure. These application methods ultimately provide a dried and cured marine coating that has a uniform distribution of the antifouling agents.

Among the various aspects of the present invention is a marine structure comprising a structural element treated with an antifouling agent as described above. The marine structure may be treated with the antifouling agent by contacting the antifouling agent with the surface or the pores of the marine structure. The marine structures that can be treated are described in more detail below. As described above the treatment with the antifouling agent provides a surface that is hole-free, flexible and resists cracking, peeling or other deformity. Once dried, the coating of the marine structure comprises a metal chelate or metal salt having a concentration from about 0.07 wt. % to about 70 wt. %; preferably, from about 0.15 wt. % to about 35 wt. %. More preferably, the metal chelate or metal salt concentration in the coating of the marine structure can be from about 0.15 wt. % to about 15 wt. %.

E. Fouling Organisms

The marine coatings of the present invention are effective for inhibiting fouling of underwater structures by a variety of organisms. Specifically, they are effective for preventing the attachment and propagation of organisms such as those described below and they provide antifouling properties over a long period of time.

Generally, barnacles, tubeworms, algae, seaweed and brown and red bryozoans are the organisms that cause the greatest concern in salt and brackish waters. Zebra mussels are the organisms that cause the most fouling problems in fresh water of temperate and subtropical areas.

The fouling organisms are those that attach to an aquatic surface. These include, for example, barnacles (members of the class Cirripedia) described below, tubeworms, sea mussels, Zebra mussels, hydroides, ectoprocts, tube-building amphipods, oysters, sea moss, mollusks, shellfish, ulba, enteromorpha, ectocorpus, ostrea, mytilus, ascidian, slime; seaweed and algae such as sea lettuce, green laver, marine spirogyra and red and brown bryozoan. The invention is contemplated to inhibit attachment of additional aquatic organisms which otherwise tend to fix themselves to a submersed surface. These organisms can include fresh and salt water environments and organisms.

Barnacles belong to the phylum Arthropoda, subphylum Crustacea, class Cirripedia. They are exclusively marine and, unlike other crustaceans, are all sessile. There are more than 600 species worldwide, and many are colorful animals, for example, red, orange, purple, pink and striped. The majority are a few centimeters in diameter, with some considerably larger. Most are found in the intertidal zone. Those living in shallow-water communities are either typical fouling balanids or commensals.

Twenty-two species of barnacles are reported in the Indian Ocean. Of these seven are frequently encountered on panels testing the efficacy of antifouling coating as described in Example 2 and harbor installations. They are *Balanus amphitrite amphitrite, Balanus amphitrite communis, Balanus uariegatus, Megabalanus antillensis, Chthamalus malayensis, Chthamalus withersi*, and *Lapas anatifera*. All these species have broad geographic ranges. All *Chthamalus* species, *Lepas* species, and *B. amphitrite* prefer waters of near normal salinities.

Marine algae vary in size from one-celled organisms a few millimeters in diameter to highly organized plants attaining a length of 30 meters. All algae capable of photosynthetic activity contain the pigment chlorophyll, which is enclosed in cell inclusions called chloroplasts. A single algal cell may contain one or more chloroplasts. Micro algae (diatoms) are major components of films formed on the surface of a marine structure as it becomes fouled and may play a role in the ecology of these films.

Diatoms belong to the class Bacillariophyceae. A major characteristic of many benthic diatoms is their ability to become permanently attached to surfaces. This is important both ecologically and economically as diatoms constitute at least a portion of the organisms that foul marine structures. For example, diatoms of the following genus (*Dunaliella, Nitzschia, Skeletonema, Chaetoceros*) and species (*Dunaliella tertiolecta, Skeletonema costatum*) are important to control.

An underwater marine structure can be any surface that is in contact with fresh, salt, estuarine, brackish, sea or other bodies of water including, for example, ship surfaces (e.g., ship hulls, boat hulls, submarine hulls, propellers, rudders, keels, centerboards, fins, hydrofoils), deck surfaces, buoys, piers, wharves, jetties, fishing nets, cooling system surfaces, cooling water intake or discharge pipes, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pipes, pumps, valves, wires, cables, ropes, ladders, pontoons, transponders, antennae, barges, periscopes, snorkels, gun mounts, gun barrels, launch tubes, mines, torpedoes and depth charges.

The methods for inhibiting fouling of an underwater marine structure use the marine coating compositions and marine coatings described above. Further, these compositions can be effective for minimizing fouling of underwater marine structures from the fouling organisms described above.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Determination of $EC_{50}$

The method of Rittschof et al. (Biofouling, 1992, Vol. 6, pp. 115-122) was followed to determine the $EC_{50}$ (i.e., the antifouling agent concentration that can be expected to cause a defined effect in 50% of a given population of organisms under defined conditions) for barnacle cyprids. In this case, the defined effect is that the cyprids have not settled and have not attached to the Petri dish. Thus, in the attached data set, the "set" column indicates the total number of cyprid larvae that have settled and attached on the surface of the Petri dish and "non-set" indicates the total number of cyprids that remain swimming in the seawater and have not settled on the surface of the Petri dish.

Briefly, the barnacle adults are cultured in the laboratory and allowed to spawn naturally. The larvae are harvested and grown in artificial culture systems until they reach the cyprid stage at which time the larvae become competent to attach to surfaces. Once attached, the cyprids transform into a pinhead barnacle, thus becoming permanently attached to the surface. Rittschof D, Clare A S, Gerhart D J, Avelin Mary, Bonavetura J (1991) Barnacle in vitro assays for biologically active substances: toxicity and settlement assays using mass cultured *Balanus amphitrite amphitrite* Darwin. Biofouling (1992) 6:115-122.

The $EC_{50}$ data are summarized as follows:

HMTBA-Zn $EC_{50}$ $5.7 \times 10^{-3}$ mg/ml

HMTBA-Cu $EC_{50}$ $1.8 \times 10^{-3}$ mg/ml

These data indicate that both compounds are biologically active as inhibitors of barnacle cyprid settlement. The HMTBA-Zn and HMTBA-Cu compounds were soluble in seawater at the levels added, so the concentration indicates the mg of solid HMTBA-Zn and HMTBA-Cu added per mL of seawater. Five replicates (e.g., a-e) for each concentration and the control were collected. At the 0.1 mg per ml, both compounds showed toxic effects on the cyprids resulting in death of all cyprids and therefore no settlement was observed. At 0.01 mg/ml and higher, the cyprids remained normal in appearance and showed normal swimming behavior patterns indicating no adverse effects. The HMTBA-Zn and HMTBA-Cu data for determining the $EC_{50}$ values are represented in Table 2 and 3 respectively.

TABLE 2

Barnacle Cyprid Assay Data, EC50 Calculations for HMTBA-Zn

| Concentration | | HMTBA-Zn | | | |
| --- | --- | --- | --- | --- | --- |
| | | Set | Non set | Total | % of set |
| Control | a | 57 | 5 | 96 | 59 |
| | b | 63 | 21 | 84 | 75 |
| | c | 49 | 7 | 56 | 88 |
| | d | 20 | 14 | 34 | 59 |
| | e | 48 | 6 | 54 | 89 |
| Total | | 237 | 53 | 324 | 73 |
| | | | | SD | 14.57 |
| | | | | SE | 6.52 |
| 0.1 mg/ml | a | 0 | 92 | 92 | 0 |
| | b | 0 | 69 | 69 | 0 |
| | c | 0 | 63 | 63 | 0 |
| | d | 0 | 58 | 58 | 0 |
| | e | 0 | 64 | 64 | 0 |
| Total | | 0 | 346 | 346 | 0 |
| | | | | SD | 0.00 |
| | | | | SE | 0.00 |
| 0.01 mg/ml | a | 21 | 49 | 70 | 30 |
| | b | 19 | 54 | 73 | 26 |
| | c | 29 | 44 | 73 | 40 |
| | d | 16 | 34 | 50 | 32 |
| | e | 14 | 26 | 40 | 35 |
| Total | | 99 | 207 | 306 | 32 |
| | | | | SD | 5.17 |
| | | | | SE | 2.31 |
| 0.001 mg/ml | a | 49 | 30 | 79 | 62 |
| | b | 49 | 14 | 63 | 78 |
| | c | 36 | 16 | 52 | 69 |
| | d | 26 | 38 | 64 | 41 |
| | e | 27 | 37 | 64 | 42 |
| Total | | 187 | 135 | 322 | 58 |
| | | | | SD | 16.47 |
| | | | | SE | 7.36 |
| 1e-4 mg/ml | a | 37 | 28 | 65 | 57 |
| | b | 31 | 21 | 52 | 60 |
| | c | 41 | 12 | 53 | 77 |
| | d | 38 | 25 | 63 | 60 |
| | e | 44 | 36 | 80 | 55 |
| Total | | 191 | 122 | 313 | 61 |
| | | | | SD | 8.93 |
| | | | | SE | 3.99 |

PROBIT ANALYSIS: Barnacle settlement vs. HMTBA-Zn DATA AS INPUT

| DOSE | NO. TESTED | NO. RESPONDING |
| --- | --- | --- |
| .1 | 346 | 346 |
| .01 | 306 | 207 |
| .001 | 322 | 135 |

TABLE 2-continued

Barnacle Cyprid Assay Data, EC50 Calculations for HMTBA-Zn

| | | |
|---|---|---|
| .0001 | 313 | 122 |
| .00001 | 312 | 97 |

| | |
|---|---|
| PROPORTION OF CONTROLS RESPONDING = | .27 |
| SLOPE = | 1.564077 |
| INTERCEPT = | 8.512927 |
| VARIANCE SLOPE = | 1.513248E−02 |
| LOG · $ED_{50}$ = | −2.246007 |
| 95% CONFIDENCE INTERVAL = | −2.14908 to 2.356471 |
| VARIANCE LOG · $ED_{50}$ = | $2.704283e^{-03}$ |
| CHI 2 = | 43.8671 |
| DF = | 3 |
| 95% CONFIDENCE INTERVAL = | $7.094474e^{-03}$ to $4.40078e^{-03}$ |
| $EC_{50}$ = | $5.675354e^{-03}$ |

TABLE 3

Barnacle Cyprid Assay Data, EC50 Calculations for HMTBA-Cu

| Concentration | Set | Non set | Total | % of set |
|---|---|---|---|---|
| Control | | | | |
| A | 54 | 12 | 66 | 82 |
| B | 51 | 17 | 68 | 75 |
| C | 42 | 19 | 61 | 69 |
| D | 64 | 11 | 75 | 85 |
| E | 49 | 16 | 65 | 75 |
| Total | 260 | 75 | 335 | 78 |
| | | | SD | 6.43 |
| | | | SE | 2.87 |
| 0.1 mg/ml | | | | |
| A | 0 | 69 | 69 | 0 |
| B | 0 | 94 | 94 | 0 |
| C | 0 | 54 | 54 | 0 |
| D | 0 | 59 | 59 | 0 |
| E | 0 | 38 | 38 | 0 |
| Total | 0 | 314 | 314 | 0 |
| | | | SD | 0.00 |
| | | | SE | 0.00 |
| 0.01 mg/ml | | | | |
| A | 8 | 79 | 87 | 9 |
| B | 4 | 66 | 70 | 6 |
| C | 5 | 59 | 64 | 8 |
| D | 8 | 25 | 33 | 24 |
| C | 5 | 56 | 61 | 8 |
| Total | 30 | 285 | 315 | 10 |
| | | | SD | 7.49 |
| | | | SE | 3.35 |
| 0.001 mg/ml | | | | |
| A | 23 | 27 | 50 | 46 |
| B | 44 | 34 | 78 | 56 |
| C | 31 | 42 | 73 | 42 |
| D | 41 | 34 | 75 | 55 |
| E | 34 | 18 | 52 | 65 |
| Total | 173 | 155 | 328 | 53 |
| | | | SD | 9.05 |
| | | | SE | 4.05 |
| 1e-4 mg/ml | | | | |
| A | 21 | 11 | 32 | 66 |
| B | 46 | 12 | 58 | 79 |
| C | 49 | 29 | 78 | 63 |
| D | 43 | 16 | 59 | 73 |
| E | 54 | 21 | 75 | 72 |
| Total | 213 | 89 | 302 | 71 |
| | | | SD | 6.49 |
| | | | SE | 2.90 |
| 1e-5 mg/ml | | | | |
| A | 46 | 14 | 60 | 77 |
| B | 48 | 21 | 69 | 70 |
| C | 42 | 15 | 57 | 74 |
| D | 54 | 25 | 79 | 68 |
| E | 51 | 11 | 62 | 82 |
| Total | 241 | 86 | 327 | 74 |
| | | | SD | 5.63 |
| | | | SE | 2.52 |

PROBIT ANALYSIS: Barnacle settlement vs. HMTBA-Cu DATA AS INPUT

| DOSE | NO. TESTED | NO. RESPONDING |
|---|---|---|
| .1 | 314 | 314 |
| .01 | 315 | 285 |
| .001 | 328 | 155 |
| .0001 | 302 | 89 |
| .00001 | 327 | 86 |

| | |
|---|---|
| PROPORTION OF CONTROLS RESPONDING = | .22 |
| SLOPE = | 1.567059 |
| INTERCEPT = | 9.303154 |
| VARIANCE SLOPE = | 1.357022E−02 |
| LOG · $ED_{50}$ = | −2.746008 |
| 95% CONFIDENCE INTERVAL = | −2.657091 to 2.844901 |
| VARIANCE LOG · $ED_{50}$ = | $2.229857e^{-03}$ |
| CHI 2 = | 9.710464 |
| DF = | 3 |
| 95% CONFIDENCE INTERVAL = | $2.202464e^{-0.3}$ to $1.429222e^{-03}$ |
| $EC_{50}$ = | $1.794702e^{-03}$ |

Example 2

Fouling Tests

HMTBA-Cu and HMTBA-Zn were supplied in powdered form by Novus International. The powder as supplied was found too large in particle size (HMTBA-Zn and HMTBA-Cu had a mean particle size of about 450 μm and 350 μm respectively) to produce satisfactory dispersion in the paints and was further ground manually to break up the larger particles. The compounds (HMTBA-Cu and HMTBA-Zn) were added to copper self-polishing copolymer (CUSP) paints, copper ablative (CUAB) paint, copper-free self-polishing (MFSP) and copper-free ablative (MFAB) paints at concentrations of 1, 3, 5 and 10% (w/w). The formulated paints were applied on PVC test panels (3 inch by 10 inch, ⅛ inch thickness), allowed to dry and shipped to a marine research center at Sacred Heart Marine Research Centre (SHMRC) in Tuticorin, India. The panels were mounted on frames on a floating platform in the open ocean and submerged totally under 3 ft of seawater for a period of 6 months, 9, or 12 months.

After the completion of the exposure period the panels were taken out of the seawater and transported to the shore laboratory in containers with seawater. The panels were evaluated by digital photography and physical examination of the coated surface. Barnacles were counted on the surface of the panels and along the edges. When there was substantial fouling on the surface, the area of the panel surface covered by barnacle fouling was estimated according to the methods described in ASTM D-3623. The panels were returned to the platform and again placed in total immersion. The panels were out of seawater during the examination for no more than 10 minutes.

Figure 1B:
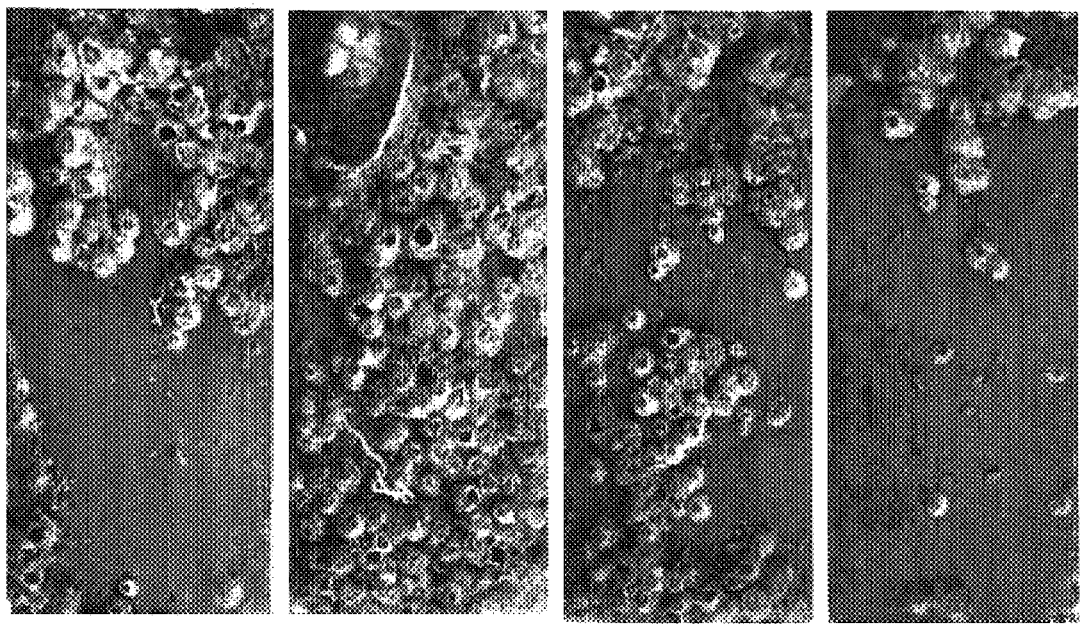
Figure 1C:
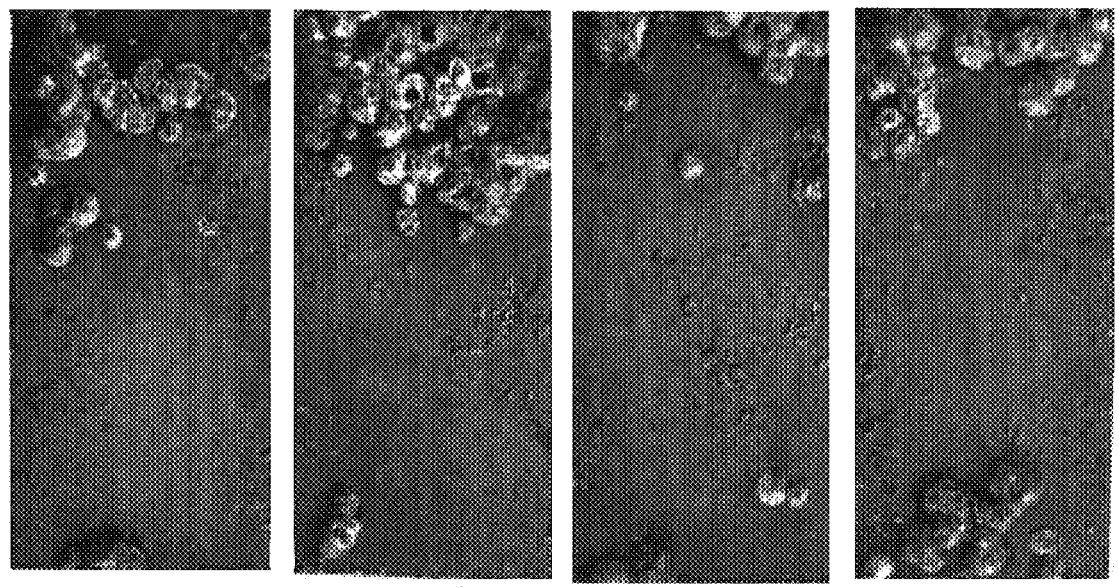
Figure 2A:
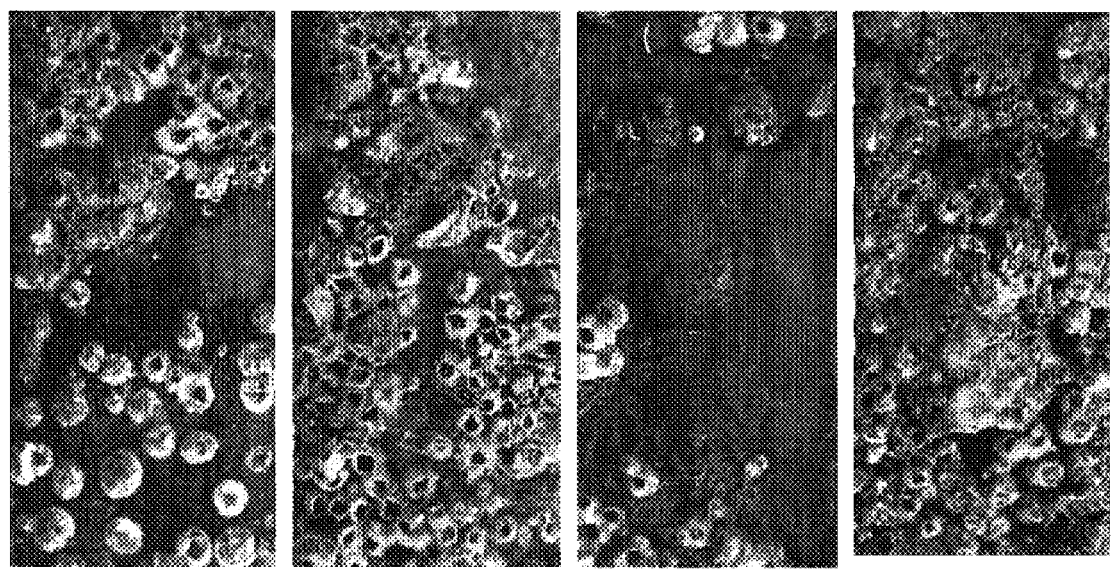
FIGS. 2(a)-(c) depict photographic images illustrating the anti-fouling activity of (a) a negative control, (b) 5% HMTBA-Cu and (c) 5% HMTBA-Zn in CUSP paint.

The barnacle counts data are summarized in Tables 4-5, FIGS. 1-2, and graphically described herein.

Six Month Immersion Tests

The reported data were extracted from the raw data as described below, and are shown as total barnacle counts for both duplicate panels of each test formulation. In Table 4, the mean and standard deviation of the data derived from the four panels' surfaces of the duplicate panels for each group. The barnacle counts along the edges were not considered in this evaluation because of the expected uneven coating and inherent tendency of barnacles to first attach to edges. In addition, coatings along the edges can be easily damaged or uneven. Thus, for evaluation purposes only the coated surfaces of the flat areas were considered for this evaluation.

Since all the test formulations in the MFSP series (metal-free self polishing coating) were fully covered by barnacles, these panels were not included in this evaluation. A similar situation was found for 5% Zinc Omadine (zinc salt of pyrithione) in MFSP coatings wherein the surfaces were fully covered by barnacles.

HMTBA-Cu and HMTBA-Zn showed significant efficacy in both copper self-polishing and metal-free ablative coatings after six months of exposure to marine organisms. In both coating systems, the paint negative controls and the positive controls (Zn-Omadine) have substantial settlement compared to all concentrations of HMTBA-Cu and HMTBA-Zn compounds. In copper ablative coatings HMTBA-ZN at 5% outperformed HMTBA-Cu, zinc-Omadine and the negative control.

Zinc Omadine was used as the positive control for this series of tests. It is important to note here that fouling is continuous throughout the year at the Tuticorin, India site and the degree of settlement is generally the same for the same coating system.

TABLE 4

Effect of various concentrations of HMTBA-Cu and HMTBA-Zn in various marine paint coatings on the settlement of barnacles (6-Month Static Immersion Testing Trial Results).

| Chemical | Coating | Concentration (%) | Total barnacle Count | Mean ± SD |
|---|---|---|---|---|
| HMTBA-Zn | CUSP | 0 | 46 | 11.5 ± 9.4 |
| | | 1 | 1 | 0.3 ± 0.4 |
| | | 3 | 0 | 0 |
| | | 5 | 0 | 0 |
| | | 10 | 2 | 0.5 ± 0.9 |
| | CUAB | 0 | 223 | 55.8 ± 56.4 |
| | | 1 | 123 | 30.8 ± 11.6 |
| | | 3 | 52 | 13.0 ± 10.7 |
| | | 5 | 1 | 0.3 ± 0.4 |
| | | 10 | 101 | 25.3 ± 2.9 |
| | MFAB | 0 | 6 | 1.5 ± 1.9 |
| | | 1 | 0 | 0 |
| | | 3 | 3 | 0.8 ± 1.3 |
| | | 5 | 1 | 0.3 ± 0.4 |
| | | 10 | 7 | 1.8 ± 1.3 |
| HMTBA-Cu | CUSP | 0 | 46 | 11.5 ± 9.4 |
| | | 1 | 4 | 1.0 ± 1.7 |
| | | 3 | 6 | 1.5 ± 2.6 |
| | | 5 | 8 | 2.0 ± 2.4 |
| | | 10 | 9 | 2.3 ± 1.9 |

TABLE 4-continued

Effect of various concentrations of HMTBA-Cu and HMTBA-Zn in various marine paint coatings on the settlement of barnacles (6-Month Static Immersion Testing Trial Results).

| Chemical | Coating | Concentration (%) | Total barnacle Count | Mean ± SD |
|---|---|---|---|---|
| | CUAB | 0 | 673 | 168.0 ± 195.0 |
| | | 1 | 472 | 118.0 ± 158.0 |
| | | 3 | 170 | 42.5 ± 21.1 |
| | | 5 | 126 | 31.4 ± 46.4 |
| | | 10 | 123 | 30.8 ± 12.9 |
| | MFAB | 0 | 6 | 1.5 ± 2.1 |
| | | 1 | 8 | 2.0 ± 2.4 |
| | | 3 | 13 | 3.3 ± 4.5 |
| | | 5 | 11 | 2.8 ± 4.2 |
| | | 10 | 4 | 1.0 ± 1.7 |
| Zn Omadine | CUSP | 5 | 33 | 8.3 ± 4.0 |
| | CUAB | 5 | 167 | 41.8 ± 23.3 |
| | MFAB | 5 | 113 | 28 ± 15.0 |

Nine Month Immersion Testing

Table 5 summarizes the anti-fouling data from the nine-month immersion test, performed as described above for the six month tests.

TABLE 5

Effect of various concentrations of HMTBA-Cu, HMTBA-Zn, copper methionine and zinc methionine in various marine paint coatings on the settlement of barnacles (Results of 9-month static immersion testing in the Indian Ocean).

| | LS MEAN BARNACLES | STANDARD ERROR |
|---|---|---|
| CUSP PAINT | | |
| Negative Control | 169.2 | 27.3 |
| HMTBA-Zn | 3 | 27.3 |
| HMTBA-Cu | 16 | 27.3 |
| Cu-Methionine | 0.5 | 27.3 |
| Zn-Methionine | 0.5 | 27.3 |
| MFAB PAINT | | |
| Negative Control | 6.5 | 16.8 |
| HMTBA-Zn | 1.5 | 16.8 |
| HMTBA-Cu | 1.25 | 16.8 |
| Cu-Methionine | 6.25 | 16.8 |
| Zn-Methionine | 8 | 16.8 |

"LS mean barnacles" represents the least squares of the means of barnacles.

Twelve Month Immersion Tests

Figure 2B:
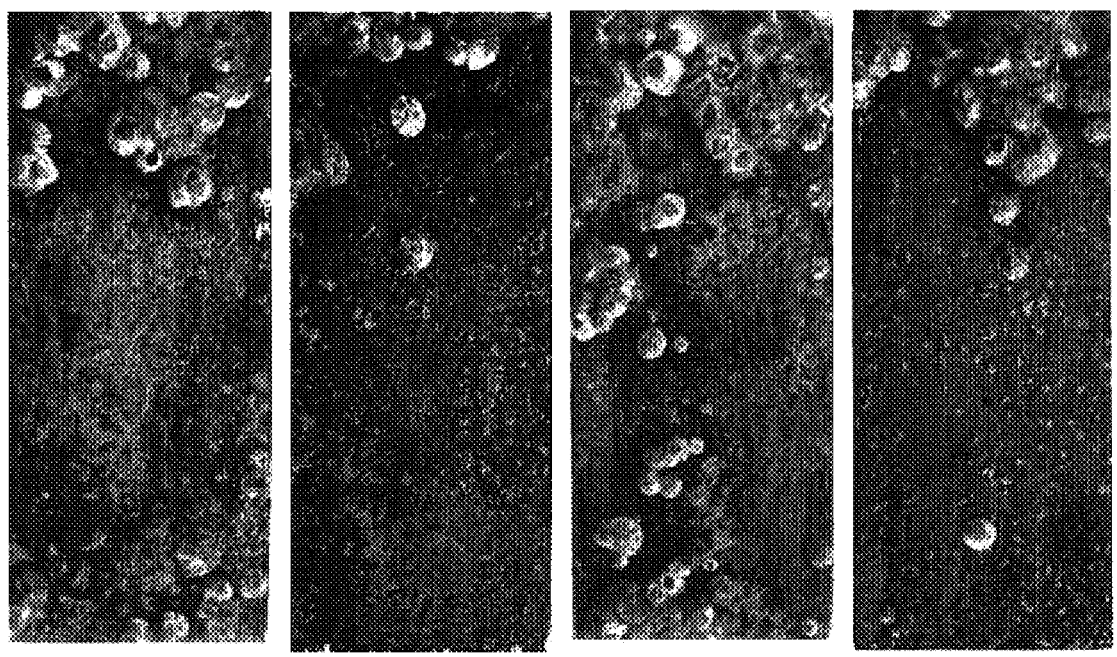
Figure 2C:
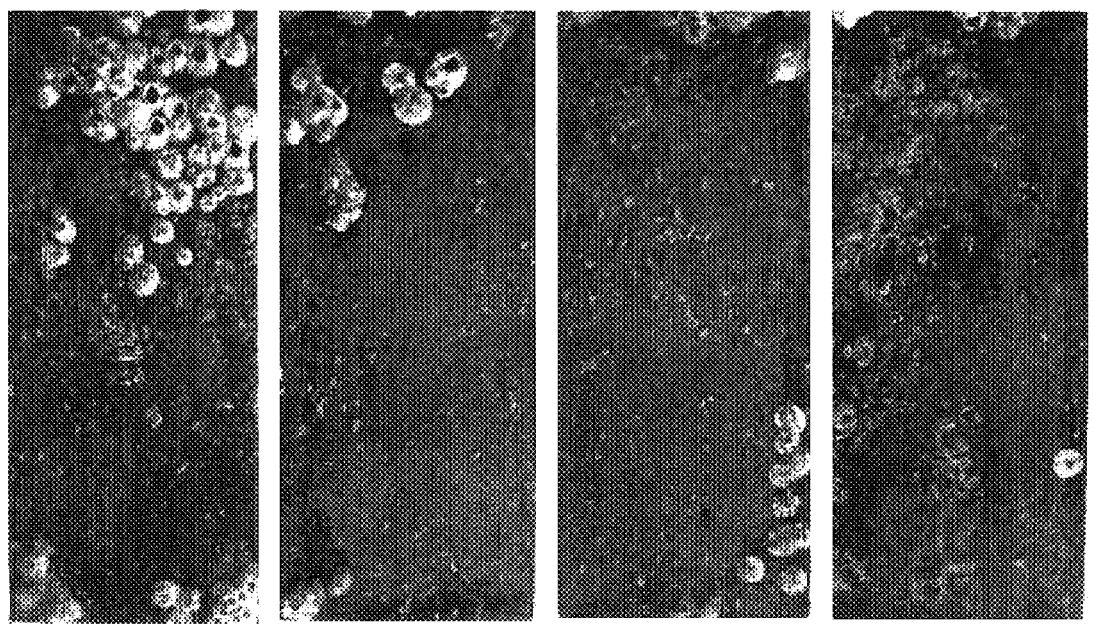

A twelve month immersion test was performed as described above for the six month tests. FIG. 1 illustrates the anti-fouling activity of HMTBA-Cu (FIG. 1b) and HMTBA-Zn (FIG. 1c) in CUAB paint, while FIG. 2 illustrates the antifouling activity of HMTBA-Cu (FIG. 2b) and HMTBA-Zn (FIG. 2c) in CUSP paint.

Fifteen Month Immersion Tests

Below are the results of a 15-month Static Immersion Test in the Indian Ocean. Two different paints were used: CuAB, i.e., Copper ablative paint and CuSP, i.e., Copper self-polishing paint. The test was performed as described above except that the antifouling reagent used was copper (II) nitrate trihydrate. For both table 6 and 7, ◆ means that yellow sponge was formed on the surface of the barnacles, ● means that red sponge was formed on the surface of the barnacles, ○ means that black sponge was formed on the surface of the barnacles, and—means that the paint was sticky in all the panels tested.

TABLE 6

Effect of various concentrations of copper (II) nitrate trihydrate in CuAB marine coatings on the settlement of barnacles (Results of 15-month static immersion testing in the Indian Ocean).

| PANEL ID | Panel Side | No. of barnacles on the coated surface | % of the surface with barnacles fouling | edge No of Barnacles | Maximum diameter in mm | No. of Oyster | No. of Tubeworms |
|---|---|---|---|---|---|---|---|
| Cu AB Copper (II) Nitrate trihydrate 5% | A | 27 | — | 3 | 10 | — | — |
|  | B♦ | 25 | — | 3 | 10 | 1 | — |
| Cu AB Copper (II) Nitrate trihydrate 5% | A♦ | 93 | — | — | 11 | 1 | — |
|  | B | 30 | — | 3 | 9 | — | — |
| Cu AB Control Paint | A♦ | — | 95 | — | 11 | 3 | 1 |
|  | B♦○ | — | 95 | — | 11 | 3 | — |
| Cu AB Control Paint | A♦○ | — | 90 | — | 12 | — | — |
|  | B♦○ | — | 95 | — | 12 | 1 | — |

TABLE 7

Effect of various concentrations of copper (II) nitrate trihydrate in CuSP marine coatings on the settlement of barnacles (Results of 15-month static immersion testing in the Indian Ocean).

| Panel ID | Panel Side | No. of barnacles on the coated surface | % of the surface with barnacles fouling | edge No of Barnacles | Maximum diameter in mm | No. of Oyster | No. of Tubeworms |
|---|---|---|---|---|---|---|---|
| Cu SP Copper (II) Nitrate trihydrate 5% | A♦ | — | 50 | — | 10 | — | — |
|  | B | 84 | — | — | 11 | — | — |
| Cu SP Copper (II) Nitrate trihydrate 5% | A♦ | — | 40 | — | 11 | — | 2 |
|  | B♦ | — | 60 | — | 10 | 2 | 1 |
| Cu SP Control Paint | A | — | 100 | — | 13 | — | 1 |
|  | B♦● | — | 75 | — | 11 | 2 | — |
| Cu SP Control Paint | A♦ | — | 60 | — | 12 | — | — |
|  | B♦ | — | 95 | — | 12 | 1 | — |

Five Month Fresh Water Immersion Tests

Figure 3A:
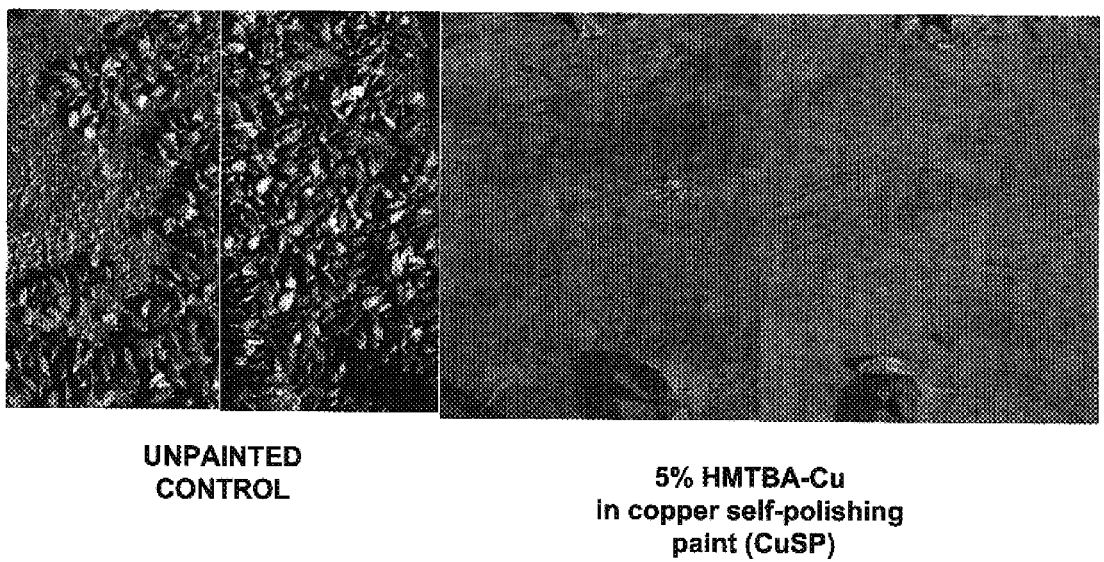
FIGS. 3(a)-(b) depict photographic images illustrating the anti-fouling activity of (a) a negative control and 5% HMTBA-Cu, and (b) a negative control and 5% HMTBA-Zn in CUSP paint.
Figure 3B:
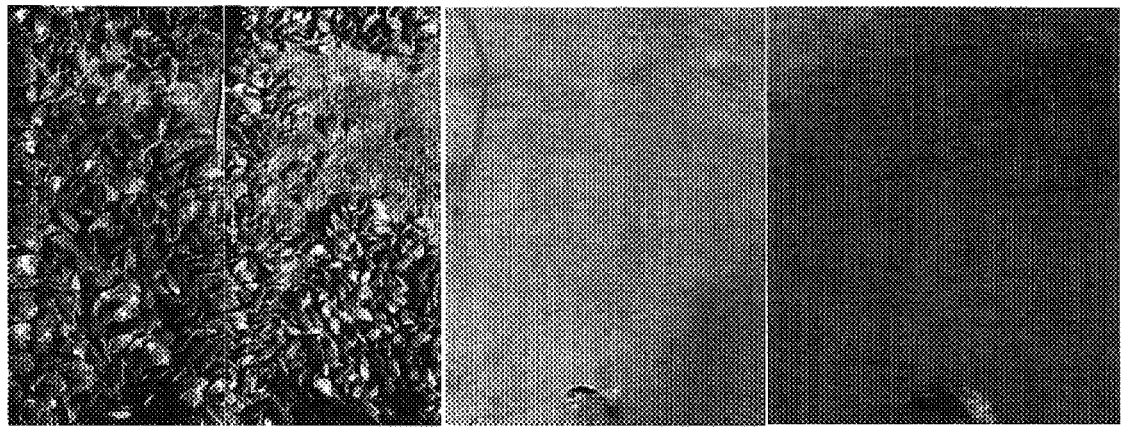
Figure 4A:
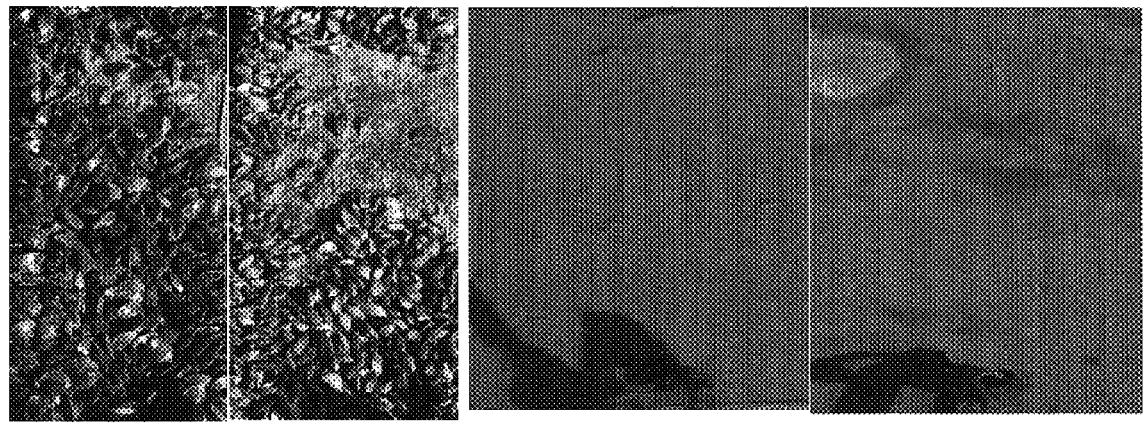
Figure 4B:
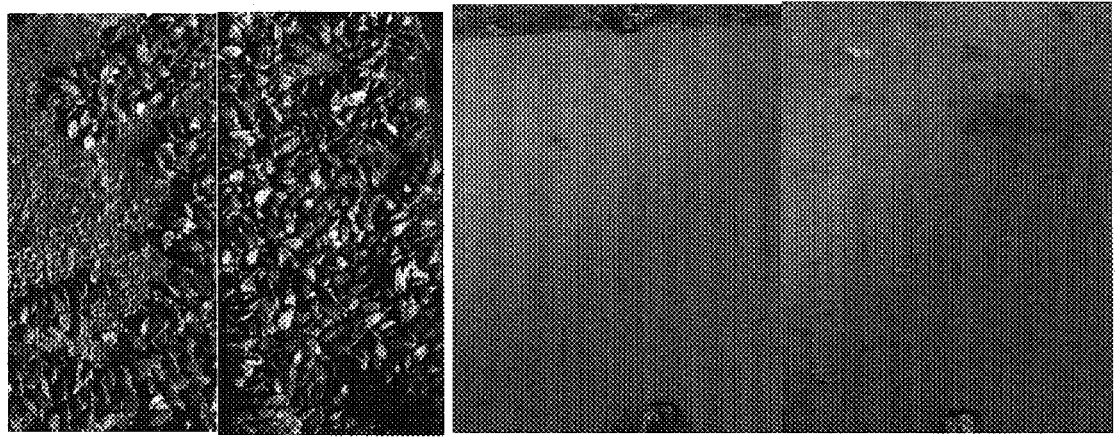

Immersion tests, similar to the ones described above, were performed in fresh water. FIG. 3 represents the anti-fouling activity of HMTBA-Cu (FIG. 3A) and HMTBA-Zn (FIG. 3B) in CUSP paint. FIG. 4 represents the anti-fouling activity of HMTBA-Cu (FIG. 4A) and HMTBA-Zn (FIG. 4B) in CUAB paint.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A marine coating composition, the composition comprising an antifouling agent and an organic vehicle, the antifouling agent comprising a metal chelate or a metal salt, the metal chelate comprising metal ions and ligands wherein a compound of formula (1) is a source of the ligands, the metal salt comprising metal ions and anions wherein a compound of formula (1) is a source of the anions, the compound of formula 1 comprising:

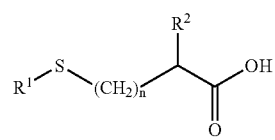

wherein:
  n is an integer from 0 to 2;
  $R^1$ is methyl or ethyl; and
  $R^2$ is selected from the group consisting of hydroxyl and amino.

2. The marine coating composition of claim 1 comprising a metal chelate, wherein the average ligand to metal ion ratio is about 2:1.

3. The marine coating composition of claim 1 comprising a metal salt, wherein the average anion to metal ion ratio is about 1:1.

4. The marine coating composition of claim 1, wherein the metal ions are selected from the group consisting of zinc ions, copper ions, manganese ions, iron ions, chromium ions, nickel ions, cobalt ions, silver ions, calcium ions and combinations thereof.

5. The marine coating composition of claim 1, wherein the metal ions comprise zinc ions or copper ions.

6. The marine coating composition of claim 1, further comprising another biocidal agent selected from the group consisting of copper nitrate, copper isothiocyanate, N'-tert-butyl-N-cyclopropyl-6-(methylthio)-1,3,5-triazine-2,4-diamine, N-dichlorofluoromethylthio-N',N'-dimethyl-N-phenylsulfamide, 3-(3,4-dichlorophenyl)-1,1-dimethylurea, 2-(thiocyanomethylthio) benzothiazole, tributyultin methacrylate copolymer, tributyltin oxide and combinations thereof.

7. The marine coating composition of claim 1, wherein n is 2, $R^1$ is methyl, and $R^2$ is hydroxyl.

8. The marine coating composition of claim 7, wherein the metal ions comprise zinc ions.

9. The marine coating composition of claim 7, wherein the metal ions comprise copper ions.

10. The marine coating composition of claim 7, wherein the metal ions comprise copper ions or zinc ions and further comprising another biocidal agent selected from the group consisting of copper nitrate, copper isothiocyanate, N'-tert-butyl-N-cyclopropyl-6-(methylthio)-1,3,5-triazine-2,4-diamine, N-dichlorofluoromethylthio-N',N'-dimethyl-N-phenylsulfamide, 3-(3,4-dichlorophenyl)-1,1-dimethylurea, 2-(thiocyanomethylthio) benzothiazole, tributyultin methacrylate copolymer, tributyltin oxide and combinations thereof.

11. The marine coating composition of claim 1, wherein the metal chelate or metal salt is present in the marine coating composition at a concentration from about 0.05 wt. % to about 50 wt. %.

12. The marine coating composition of claim 1, wherein the metal chelate or metal salt is present in the marine coating composition at a concentration from about 0.1 wt. % to about 25 wt. %.

13. The marine coating composition of claim 1, wherein the metal chelate or metal salt is present in the marine coating composition at a concentration from about 1 wt. % to about 10 wt. %.

14. The marine coating composition of claim 1, wherein a mean particle size of the metal chelate or metal salt is from about 0.5 μm to about 600 μm.

15. The marine coating composition of claim 1, wherein a mean particle size of the metal chelate or metal salt is from about 300 to about 500 μm.

16. The marine coating composition of claim 1, wherein a mean particle size of the metal chelate or metal salt is from about 0.5 μm to about 25 μm.

17. The marine coating composition of claim 1, wherein the organic vehicle is selected from the group consisting of resins, diluents and combinations thereof.

18. The marine coating composition of claim 17, wherein the resin is selected from the group consisting of natural resins, synthetic resins and combinations thereof.

19. The marine coating composition of claim 17, wherein the resin is selected from the group consisting of acrylic resins, copolymers of vinyl chloride, vinyl isobutyl ether, carboxylic acid functional polymers, vinyl resins, alkyd resins, epoxy resins, acrylic resins, polyurethane resins, polyester resins, vinyl acrylic resins, vinyl esters and combinations thereof.

20. The marine coating composition of claim 1, wherein the organic vehicle is a resin selected from the group consisting of self-polishing copolymer resins, ablative resins, leaching resins and combinations thereof.

21. The marine coating composition of claim 1, wherein the organic vehicle is a diluent selected from the group consisting of alcohols, aliphatic, cycloaliphatic and aromatic hydrocarbons, ketones, ether alcohols, esters, chlorinated hydrocarbons and combinations thereof.

22. The marine coating composition of claim 21, wherein the diluent is selected from the group consisting of methanol, ethanol, propanol, isopropanol, butanol, isobutanol, benzyl alcohol, white spirit, cyclohexane, toluene, xylene, naphthalene, methyl ethyl ketone, acetone, methyl isobutyl ketone, methyl isoamyl ketone, diacetone alcohol, cyclohexanone, 2-butoxyethanol, propylene glycol monomethyl ether, butyl diglycol, methoxypropyl acetate, n-butyl acetate, 2-ethoxyethyl acetate, methylene chloride, tetrachloroethane, trichloroethylene and combinations thereof.

23. The marine coating composition of claim 1, wherein the composition further comprises an additive selected from the group consisting of swelling agents, pigments, wetting agents, fillers and combinations thereof.

24. The marine coating composition of claim 23, comprising an organic vehicle comprising a resin and a diluent; the resin selected from the group consisting of rosins, acrylic resins, copolymers of vinyl chloride, vinyl isobutyl ether, carboxylic acid functional polymers, vinyl resins, alkyd resins, epoxy resins, acrylic resins, polyurethane resins, polyester resins, vinyl acrylic resins, vinyl esters and combinations thereof; the diluent selected from the group consisting of alcohols, aliphatic, cycloaliphatic and aromatic hydrocarbons, ketones, ether alcohols, esters, chlorinated hydrocarbons and combinations thereof; an additive selected from the group consisting of pigments, fillers, swelling agents, wetting agents, biocides and combinations thereof; and an antifouling agent comprising zinc ions complexed with 2-hydroxy-4-methylthiobutanoic acid.

25. The marine coating composition of claim 24, wherein the diluent is selected from the group consisting of methanol, ethanol, propanol, isopropanol, butanol, isobutanol, benzyl alcohol, white spirit, cyclohexane, toluene, xylene, naphthalene, methyl ethyl ketone, acetone, methyl isobutyl ketone, methyl isoamyl ketone, diacetone alcohol, cyclohexanone, 2-butoxyethanol, propylene glycol monomethyl ether, butyl diglycol, methoxypropyl acetate, n-butyl acetate, 2-ethoxyethyl acetate, methylene chloride, tetrachloroethane, trichloroethylene and combinations thereof.

26. The marine coating composition of claim 24, wherein the concentration of the resin is from about 10 wt. % to about 35 wt. %, the concentration of the additive is from about 30 wt. % to about 60 wt. %, the concentration of the diluent is from about 15 wt. % to about 50 wt. %, and the concentration of the antifouling agent is from about 0.1 wt. % to about 10 wt. %.

27. The marine coating composition of claim 1, further comprising copper nitrate.

28. The marine coating composition of claim 1, further comprising a substituted 1,2-dihydroquinoline compound comprising Formula (II):

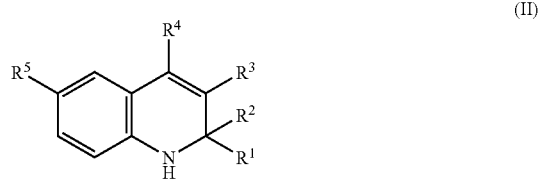

wherein:
R¹, R², R³ and R⁴ are independently selected from the group consisting of hydrogen and an alkyl group having from 1 to about 6 carbons; and
R⁵ is an alkoxy group having from 1 to about 12 carbons.

29. The marine coating of claim 28, wherein the substituted 1,2-dihydroquinolin comprises a compound wherein:
R¹, R², R³ and R⁴ are independently selected from the group consisting of hydrogen and an alkyl group having from 1 to about 4 carbons; and
R⁵ is an alkoxy group having from 1 to about 4 carbons.

30. The marine coating composition of claim 28, wherein the substituted 1,2-dihydroquinoline is 6-ethoxy-1,2-dihydro-2,2,4-trimethylquinoline.

31. The marine coating composition of claim 1, further comprising a metal chelate comprised of metal ions selected from the group consisting of zinc ions, copper ions, manganese ions, iron ions, chromium ions, silver ions, cobalt ions, calcium ions and combinations thereof; and an amino acid ligand selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs.

32. The marine coating composition of claim 1, further comprising a marine paint.

33. A method for inhibiting fouling of a marine structure, the method comprising applying a marine coating composition comprising an antifouling agent and an organic vehicle to the marine structure, the antifouling agent comprising a metal chelate or a metal salt, the metal chelate comprising metal ions and ligands wherein a compound of formula 1 is a source of the ligands, the metal salt comprising metal ions and anions wherein a compound of formula 1 is a source of said anions, the compound of formula 1 comprising:

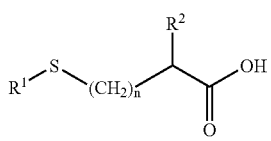

wherein:
n is an integer from 0 to 2;
R¹ is methyl or ethyl; and
R² is selected from the group consisting of hydroxyl and amino.

34. The method of claim 33, wherein the antifouling agent comprises a metal chelate having an average ligand to metal ion ratio of about 2:1.

35. The method of claim 33, wherein the antifouling agent comprises a metal salt having an average anion to metal ion ratio of about 1:1.

36. The method of claim 33, wherein the metal ions are selected from the group consisting of zinc ions, copper ions, manganese ions, iron ions, chromium ions, silver ions, cobalt ions, calcium ions and combinations thereof.

37. The method of claim 33, wherein the metal ions comprise zinc ions.

38. The method of claim 33, wherein the metal ions comprise copper ions.

39. The method of claim 33, wherein n is 2, R¹ is methyl and R² is hydroxyl.

40. The method of claim 39, wherein the metal ions comprise zinc ions.

41. The method of claim 39, wherein the metal ions comprise copper ions.

42. The method of claim 33, wherein the marine coating composition further comprises another biocidal agent selected from the group consisting of copper isothiocyanate, N'-tert-butyl-N-cyclopropyl-6-(methylthio)-1,3,5-triazine-2,4-diamine, N-dichlorofluoromethylthio-N',N'-dimethyl-N-phenylsulfamide, 3-(3,4-dichlorophenyl)-1,1-dimethylurea, 2-(thiocyanomethylthio) benzothiazole, tributyltin methacrylate copolymer, tributyltin oxide and combinations thereof.

43. The method of claim 33, wherein the marine coating composition further comprises copper nitrate.

44. The method of claim 33, wherein the marine coating composition further comprises a substituted 1,2-dihydroquinoline compound comprising Formula (II):

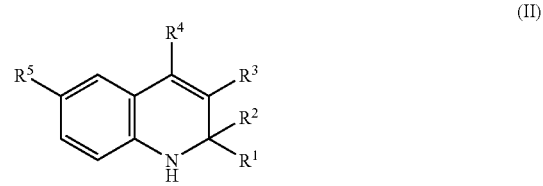

wherein:
R¹, R², R³ and R⁴ are independently selected from the group consisting of hydrogen and an alkyl group having from 1 to about 6 carbons; and
R⁵ is an alkoxy group having from 1 to about 12 carbons.

45. The method of claim 44, wherein the substituted 1,2-dihydroquinoline comprises a compound wherein:
R¹, R², R³ and R⁴ are independently selected from the group consisting of hydrogen and an alkyl group having from 1 to about 4 carbons; and
R⁵ is an alkoxy group having from 1 to about 4 carbons.

46. The method of claim 44, wherein the substituted 1,2-dihydroquinoline is 6-ethoxy-1,2-dihydro-2,2,4-trimethylquinoline.

47. The method of claim 33, wherein the marine coating composition further comprises a metal chelate comprised of metal ions selected from the group consisting of zinc ions, copper ions, manganese ions, iron ions, chromium ions, silver ions, cobalt ions, calcium ions and combinations thereof; and an amino acid ligand selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs.

48. The method of claim 33, wherein the metal chelate or metal salt is present in the antifouling marine coating composition at a concentration of from about 0.05 wt. % to about 50 wt. %.

49. The method of claim 33, wherein the metal chelate or metal salt is present in the marine coating marine coating composition at a concentration of from about 0.1 wt. % to about 25 wt. %.

50. The method of claim 33, wherein said metal chelate or metal salt is present in said marine coating marine coating composition at a concentration of from about 1 wt. % to about 10 wt. %.

51. The method of claim 33, wherein a mean particle size of the metal chelate or metal salt is from about 0.5 μm to about 600 μm.

52. The method of claim 33, wherein a mean particle size of the metal chelate or metal salt is from about 300 to about 500 μm.

53. The method of claim 33, wherein a mean particle size of the metal chelate or metal salt is from about 0.5 μm to about 25 μm.

54. The method of claim 33, wherein the marine structure is selected from the group consisting of ship hulls, boat hulls, submarine hulls, propellers, rudders, keels, centerboards, fins, hydrofoils, deck surfaces, buoys, piers, wharves, jetties, fishing nets, cooling system surfaces, cooling water intake or discharge pipes, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pumps, valves, wires, cables, ropes, ladders, pontoons, transponders, antennae, barges, periscopes, snorkels, gun mounts, gun barrels, launch tubes, mines, torpedoes and depth charges.

55. The method of claim 54, wherein the submersible marine structure comprises a ship hull.

56. The method of claim 33, wherein the antifouling agent inhibits fouling by an organism selected from the group consisting of barnacles, *Balanus amphitrite* Darwin, Zebra mussels, tubeworms, and oysters.

57. The method of claim 33, wherein the antifouling agent inhibits fouling by an organism selected from the group consisting of algae, bacteria, and a biofilm.

58. The method of claim 33, wherein the organic vehicle is selected from the group consisting of resins and diluents.

59. The method of claim 33, wherein the marine coating composition comprises paint.

60. A marine structure, the marine structure comprising a structural element and a marine coating, the marine coating comprising an antifouling agent and a resin, the antifouling agent comprising a metal chelate or a metal salt, the metal chelate comprising metal ions and ligands wherein a compound of formula 1 is a source of the ligands, the metal salt comprising metal ions and anions wherein a compound of formula 1 is a source of the anions, the compound of formula 1 comprising:

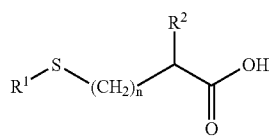

1 wherein
n is an integer from 0 to 2;
$R^1$ is methyl or ethyl; and
$R^2$ is selected from the group consisting of hydroxyl and amino.

61. The marine structure of claim 60, comprising a metal chelate wherein the average ligand to metal ion ratio is about 2:1.

62. The marine structure of claim 60, comprising a metal salt wherein the average anion to metal ion ratio is about 1:1.

63. The marine structure of claim 60, wherein the metal ions are selected from the group consisting of zinc ions, copper ions, manganese ions, iron ions, chromium ions, silver ions, cobalt ions, calcium ions and combinations thereof.

64. The marine structure of claim 60, wherein the metal ions comprise zinc ions.

65. The marine structure of claim 60, wherein the metal ions comprise copper ions.

66. The marine structure of claim 60, wherein $R^1$ is methyl, n is 2 and $R^2$ is hydroxyl.

67. The marine structure of claim 66, wherein the metal ions comprise zinc ions.

68. The marine structure of claim 66, wherein the metal ions comprise copper ions.

69. The marine structure of claim 60, wherein the marine coating further comprises another biocidal agent selected from the group consisting of copper isothiocyanate, N'-tert-butyl-N-cyclopropyl-6-(methylthio)-1,3,5-triazine-2,4-diamine, N-dichlorofluoromethylthio-N',N'-dimethyl-N-phenylsulfamide, 3-(3,4-dichlorophenyl)-1,1-dimethylurea, 2-(thiocyanomethylthio) benzothiazole, tributyltin methacrylate copolymer, tributyltin oxide and combinations thereof.

70. The marine structure of claim 60, wherein the marine coating further comprises copper nitrate.

71. The marine structure of claim 60, wherein the marine coating further comprises a substituted 1,2-dihydroquinoline compound comprising Formula (II):

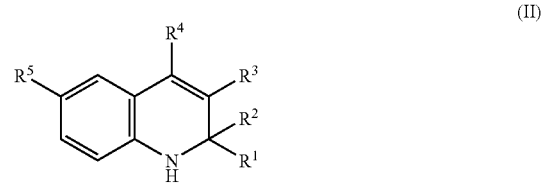

(II)

wherein:
$R^1$, $R^2$, $R^3$ and $R^4$ are independently selected from the group consisting of hydrogen and an alkyl group having from 1 to about 6 carbons; and
$R^5$ is an alkoxy group having from 1 to about 12 carbons.

72. The marine structure of claim 71, wherein the substituted 1,2-dihydroquinoline comprises a compound wherein:
$R^1$, $R^2$, $R^3$ and $R^4$ are independently selected from the group consisting of hydrogen and an alkyl group having from 1 to about 4 carbons; and
$R^5$ is an alkoxy group having from 1 to about 4 carbons.

73. The marine structure of claim 71, wherein the substituted 1,2-dihydroquinoline is 6-ethoxy-1,2-dihydro-2,2,4-trimethylquinoline.

74. The marine structure of claim 60, wherein the marine coating further comprises a metal chelate comprised of metal ions selected from the group consisting of zinc ions, copper ions, manganese ions, iron ions, chromium ions, silver ions, cobalt ions, calcium ions and combinations thereof; and an amino acid ligand selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs.

75. The marine structure of claim 60, wherein a mean particle size of the metal chelate or metal salt is from about 0.5 μm to about 600 μm.

76. The marine structure of claim 60, wherein a mean particle size of the metal chelate or metal salt is from about 300 to about 500 μm.

77. The marine structure of claim 60, wherein a mean particle size of the metal chelate or metal salt is from about 0.5 μm to about 25 μm.

78. The marine structure of claim 60, wherein the marine coating is disposed on a surface of the structural element and/or contained in pores of the structural element.

79. The marine structure of claim 60, wherein the metal chelate or metal salt is present in the marine coating at a concentration of from about 0.07 wt. % to about 70 wt. % solids weight.

80. The marine structure of claim 60, wherein the metal chelate or metal salt is present in the marine coating at a concentration of from about 0.15 wt. % to about 35 wt. % solids weight.

81. The marine structure of claim 60, wherein said metal chelate or metal salt is present in the marine coating at a concentration of from about 0.15 wt. % to about 15 wt. % solids weight.

82. The marine structure of claim 60, wherein the resin is selected from the group consisting of natural resins, synthetic resins and combinations thereof.

83. The marine structure of claim 60, wherein the resin is selected from the group consisting of rosins, acrylic resins, copolymers of vinyl chloride, vinyl isobutyl ether, carboxylic acid functional polymers, vinyl resins, alkyd resins, epoxy resins, acrylic resins, polyurethane resins, polyester resins, vinyl acrylic resins, vinyl esters and combinations thereof.

84. The marine structure of claim 60, wherein the resin is selected from the group consisting of self-polishing copolymer resins, ablative resins, leaching resins and combinations thereof.

85. The marine structure of claim 60, wherein the structural element is selected from the group consisting of ship hulls, boat hulls, submarine hulls, propellers, rudders, keels, centerboards, fins, hydrofoils, deck surfaces, buoys, piers, wharves, jetties, fishing nets, cooling system surfaces, cooling water intake or discharge pipes, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pumps, valves, wires, cables, ropes, ladders, pontoons, transponders, antennae, barges, periscopes, snorkels, gun mounts, gun barrels, launch tubes, mines, torpedoes and depth charges.

86. A marine coating composition, the composition comprising an antifouling agent and an organic vehicle, the antifouling agent comprising a metal chelate comprised of metal ions selected from the group consisting of zinc ions, copper ions, manganese ions, iron ions, chromium ions, silver ions, cobalt ions, and calcium ions; and an amino acid ligand selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs.

87. The marine coating composition of claim 86, wherein the metal ions are zinc ions or copper ions.

\* \* \* \* \*